(12) United States Patent
Heydari et al.

(10) Patent No.: US 11,278,226 B2
(45) Date of Patent: Mar. 22, 2022

(54) IMPLANTABLE ELECTROCORTICOGRAM BRAIN-COMPUTER INTERFACE SYSTEM FOR RESTORING EXTREMITY MOVEMENT

(71) Applicants: The Regents of the University of California, Oakland, CA (US); University of Southern California, Los Angeles, CA (US)

(72) Inventors: Payam Heydari, Irvine, CA (US); Zoran Nenadic, Irvine, CA (US); An Do, Orange, CA (US); Charles Liu, Los Angeles, CA (US)

(73) Assignees: THE REGENTS OF THE UNIVERSITY OF CALIFORNIA, Oakland, CA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 101 days.

(21) Appl. No.: 16/376,831

(22) Filed: Apr. 5, 2019

(65) Prior Publication Data

US 2019/0231204 A1 Aug. 1, 2019

Related U.S. Application Data

(63) Continuation-in-part of application No. PCT/US2017/055652, filed on Oct. 6, 2017.
(Continued)

(51) Int. Cl.
*A61F 2/72* (2006.01)
*A61B 5/24* (2021.01)
(Continued)

(52) U.S. Cl.
CPC .................. *A61B 5/24* (2021.01); *A61B 5/30* (2021.01); *A61B 5/6868* (2013.01); *G06F 3/00* (2013.01);
(Continued)

(58) Field of Classification Search
CPC ............ A61B 5/04001; A61B 5/04004; A61B 5/6868; A61B 5/0476; A61B 5/04851;
(Continued)

(56) References Cited

U.S. PATENT DOCUMENTS

| 7,901,368 B2 | 3/2011 | Flaherty et al. |
| 2005/0090756 A1 | 4/2005 | Wolf et al. |

(Continued)

FOREIGN PATENT DOCUMENTS

WO WO2015095182 A1 6/2015

OTHER PUBLICATIONS

A. Mahajan et al. "A 64-Channel Ultra-Low Power Bioelectric Signal Acquisition System for Brain-Computer Interface." in Proc. IEEE Biomed. Circuits Syst. Conf., 2015, pp. 1-4.
(Continued)

*Primary Examiner* — Jerrah Edwards
*Assistant Examiner* — Aren Patel
(74) *Attorney, Agent, or Firm* — Nguyen Tarbet LLC

(57) ABSTRACT

A fully-implantable brain-computer interface cyber-physical system capable of acquiring and analyzing electrocorticogram ("ECoG") signals, recorded directly from the subdural space of the brain, to enable direct brain control of a prosthetic (e.g., a robotic gait exoskeleton or a functional electrical stimulation ("FES") system) is disclosed. The present system comprises a plurality of electrodes, for acquiring the ECoG signals, and a digital signal processor ("DSP") for deriving a plurality of real-time commands from the ECoG signals. These real-time commands may then be wirelessly transmitted to the prosthetic for execution. Further, to avoid wireless data transmission of the ECoG signals from the plurality of electrodes to the DSP, which would expose the brain, skull, and scalp tissue to potentially harmful radio frequencies, a subcutaneous tunneling cable operatively couples the plurality of electrodes and the DSP.

17 Claims, 29 Drawing Sheets
(17 of 29 Drawing Sheet(s) Filed in Color)

Related U.S. Application Data

(60) Provisional application No. 62/405,021, filed on Oct. 6, 2016.

(51) Int. Cl.
    *G06F 3/00*         (2006.01)
    *G06F 3/01*         (2006.01)
    *A61B 5/30*         (2021.01)
    *A61B 5/00*         (2006.01)
    *A61B 5/369*       (2021.01)
    *A61N 1/05*         (2006.01)

(52) U.S. Cl.
CPC .............. *G06F 3/01* (2013.01); *G06F 3/015* (2013.01); *A61B 5/369* (2021.01); *A61B 5/4851* (2013.01); *A61B 5/7225* (2013.01); *A61F 2/72* (2013.01); *A61H 2201/165* (2013.01); *A61N 1/0534* (2013.01)

(58) Field of Classification Search
CPC ........... A61B 5/7225; A61B 5/72; G06F 3/00; G06F 3/01; G06F 3/015; A61H 2201/165; A61N 1/0534
See application file for complete search history.

(56) References Cited

U.S. PATENT DOCUMENTS

| | | | |
|---|---|---|---|
| 2008/0290944 A1 | 11/2008 | Sarpeshkar et al. | |
| 2008/0294062 A1 | 11/2008 | Rapoport et al. | |
| 2008/0294579 A1* | 11/2008 | Rapoport ........... | G06K 9/00536 706/12 |
| 2010/0145222 A1* | 6/2010 | Brunnett .............. | A61N 1/3605 600/554 |
| 2012/0123289 A1* | 5/2012 | Sorenson ............. | A61B 5/0031 600/544 |
| 2014/0180052 A1* | 6/2014 | Lo .......................... | A61B 5/375 600/377 |
| 2017/0070094 A1* | 3/2017 | Corum ................ | A61B 5/02055 |
| 2017/0164863 A1* | 6/2017 | Kennedy ................ | A61B 5/291 |
| 2017/0333712 A1* | 11/2017 | Chen ........................ | A61B 5/24 |

OTHER PUBLICATIONS

J. L. Collinger et al., "High-performance neuroprosthetic control by an individual with tetraplegia," The Lancet, vol. 381, No. 9866, pp. 557-564, 2013.

R. Muller, S. Gambini, and J. M. Rabaey, "A 0.013 mm2, 5 μW, DC-coupled neural signal acquisition IC with 0.5 V supply," IEEE J. Solid-State Circuits, vol. 47, No. 1, pp. 232-243, 2012.

G. Schalk and E. C. Leuthardt, "Brain-computer interfaces using electrocorticographic signals," IEEE Reviews Biomed. Eng., vol. 4, pp. 140-154, 2011.

Kim S, Tathireddy P, Normann RA, Solzbacher F. Thermal impact of an active 3-D microelectrode array implanted in the brain. IEEE Transactions on Neural Systems and Rehabilitation Engineering. 2007;15(4):493-501.

M. Daliri and M. Maymandi-Nejad, "Ultra-low voltage common-mode voltage detector circuit," Electronics Letters, vol. 44, No. 13, pp. 782-783, 2008.

W. Wattanapanitch, M. Fee, and R. Sarpeshkar, "An energy-efficient micropower neural recording amplifier," IEEE Trans. Biomed. Circuits Syst., vol. 1, No. 2, pp. 136-147, Jun. 2007.

N. Verma, et al., "A micro-power eeg acquisition soc with integrated feature extraction processor for a chronic seizure detection system," IEEE J. Solid-State Circuits, vol. 45, No. 4, pp. 804-816, Apr. 2010.

T. Denison et al., "A 2 μw 100 nv/rthz chopper-stabilized instrumentation amplifier for chronic measurement of neural field potentials," IEEE J. Solid-State Circuits, vol. 42, No. 12, pp. 2934-2945, 2007.

McCrimmon, et al., "Electrocorticographic Encoding of Human Gait in the Leg Primary Motor Cortex," Cerebral Cortex, Jul. 2017.

NeuroPace, Inc., "How the RNS® System Works," http://www.neuropace.com/the-rns-system/.

Karimi-Bidhendi et al. "CMOS Ultralow Power Brain Signal Acquisition Front-Ends: Design and Human Testing" IEEE Transactions on Biomedical Circuits and Systems, No. 99, pp. 1-12, Aug. 2017.

National Spinal Cord Injury Statistical Center (NSCIS). Spinal cord injury facts and figures at a glance—2013;. National Spinal Cord Injury Statistical Center, Birmingham, Alabama.

Ball T, Kern M, Mutschler I, Aertsen A, Schulze-Bonhage A. Signal quality of simultaneously recorded invasive and non-invasive EEG. NeuroImage. 2009; 46(3): 708-716.

Brain Products GmbH. actiCAP. http://www.brainproducts.com/productdetails.php?id=4.

NeXus-32—Mind Media. Biofeedback and Neurofeedback Systems. http://www.mindmedia.info/CMS2014/en/products/systems/nexus-32.

g.SAHARAsys. http://www.gtec.at.

Wang PT, King CE, Schombs A, Lin JJ, Sazgar M, Hsu FPK, Shaw SJ, Millett DE, Liu CY, Chui LA, Nenadic Z, Do AH. Electrocorticographic gamma band power encodes the velocity of upper extremity movements. In: Proceedings of the Fifth International Brain-Computer Interface Meeting 2013. Graz University of Technology Publishing House; 2013. p. ArticieID 120.

Do AH, Wang PT, King CE, Schombs A, Lin JJ, Sazgar M, Hsu FPK, Shaw SJ, Millett DE, Liu CY, Szymanska AA, Chui LA, Nenadic Z. Sensitivity and Specificity of Upper Extremity Movements Decoded from Electrocorticogram. In: Proc. of the 35th Annual International Conference of the IEEE Engineering in Medicine and Biology Society; 2013. p. 5618-5621.

Hochberg LR, Bacher 0, Jarosiewicz B, Masse NY, Simeral JD, Vogel J, et al. Reach and grasp by people with tetraplegia using a neurally controlled robotic arm. Nature. 2012;485(7398) :372-375.

Hochberg LR, Serruya MD, Friehs GM, Mukand JA, Saleh M, Caplan AH, et al. Neuronal ensemble control of prosthetic devices by a human with tetraplegia. Nature. 2006;442(7099) :164-171 .

Rousche PJ, Normann RA. Chronic recording capability of the Utah Intracortical Electrode Array in cat sensory cortex. J Neurosci Methods. 1998;82(1):1-15.

Schmidt S, Horch K, Normann R. Biocompatibility of silicon-based electrode arrays implanted in feline cortical tissue. J Biomed Mater Res. 1993;27(11):1393-1399.

Borton DA, Yin M, Aceros J, Nurmikko A. An implantable wireless neural interface for recording cortical circuit dynamics in moving primates. Journal of Neural Engineering. 2013;10(2):026010.

Anderson GS, Harrison RR. Wireless integrated circuit for the acquisition of electrocorticogram signals. In: Proceedings of 2010 IEEE International Symposium on Circuits and Systems (ISCAS) . IEEE; 2010. p. 2952-2955.

Hirata M, Matsushita K, Suzuki T, Yoshida T, Morris S, Yanagisawa T, et al. A fully-implantable wireless system for human brain-machine interfaces using brain surface electrodes: W-HERBS. IEICE transactions on communications. 2011 ;94(9):2448-2453.

Repacholi MH, Lerchl A, Roosli M, Sienkiewicz Z, Auvinen A, Breckenkamp J, et al. Systematic review of wireless phone use and brain cancer and other head tumors. Bioelectromagnetics. 2012;33(3):187-206.

La Fougere C, Zwergal A, Rominger A, Forster S, Fesl G, Dieterich M, et al. Real versus imagined locomotion: A 18F-FDG PET-fMRI comparison. Neuroimage. 2010;50(4) :1589-1598.

Collinger JL, Boninger ML, Bruns TM, Curley K, Wang W, Weber OJ. Functional priorities, assistive technology, and brain-computer interfaces after spinal cord injury. Journal of Rehabilitation Research & Development. 2013;50(2).

Szmigielski S. Cancer risks related to low-level RF/MW exposures, including cell phones. Electromagnetic Biology and Medicine. 2013;32(3):273-280.

Javid B, Heydari P. A 4-bit 12GS/s data acquisition System-on-Chip including a flash ADC and 4-channel DeMUX in 130nm CMOS. In: IEEE Custom Integrated Circuits Conference (CICC) ; 2012. p. 1-4.

(56) References Cited

OTHER PUBLICATIONS

C.E. King, P.T. Wang, C.M. McCrimmon, C.C.Y. Chou, A.H. Do, and Z. Nenadic, The feasibility of a brain-computer interface functional electrical stimulation system for the restoration of overground walking after paraplegia, J. NeuroEng. Rehabil., vol. 12(80), 2015.
A.H. Do, P.T. Wang, C.E. King, S.N. Chun, and Z. Nenadic, Brain-computer interface controlled robotic gait orthosis, J. NeuroEng. Rehabil., vol. 10(111), 2013.
C.E. King, P.T. Wang, L.A. Chui, A.H. Do, and Z. Nenadic, Operation of a brain-computer interface walking simulator for individuals with spinal cord injury, J. NeuroEng. Rehabil., vol. 10(77), 2013.
P.T. Wang, C.E. King, L.A. Chui, A.H. Do, and Z. Nenadic, Self-paced brain-computer interface control of ambulation in a virtual reality environment, J. Neural Eng., vol. 9(5), pp. 056016, 2012.
P.T. Wang, E.J. Puttock, C.E. King, A. Schombs, J.J. Lin, M. Sazgar, F.P.K. Hsu, S.J. Shaw, D.E. Millett, C.Y. Liu, L.A. Chui, A.H. Do, and Z. Nenadic, State and trajectory decoding of upper extremity movements from electrocorticogram, in Proc. of the 6th Annual International IEEE EMBS Conference on Neural Engineering, pp. 969-972, 2013.
International Search Report Issued for PCT Application No. PCT/US17/55652 dated Dec. 22, 2017.

\* cited by examiner

TABLE I
AMPLIFIER I DEVICE SIZES AND OPERATING POINTS

| Devices | W/L ($\mu m/\mu m$) | $I_D$ (nA) | $g_m/I_D$ ($V^{-1}$) |
|---|---|---|---|
| $M_{1a}$-$M_{1b}$ | 53.5/1.35 | 130 | 34 |
| $M_{2a}$-$M_{2b}$ | 50/10 | 65 | 25 |
| $M_{3a}$-$M_{3b}$ | 50/10 | 65 | 25 |
| $M_{4a}$-$M_{4b}$ | 3.7/32 | 1.5 | 25 |
| $M_{5a}$-$M_{5b}$ | 140/1.2 | 138 | 29 |
| $M_{6a}$-$M_{6b}$ | 15/30 | 69 | 28 |
| $M_{7a}$-$M_{7b}$ | 15/30 | 69 | 28 |
| $M_{8a}$-$M_{8b}$ | 0.4/40 | 1.5 | 26 |
| $M_9$ | 80/0.36 | 89 | 34 |
| $M_{10}$ | 80/0.36 | 170 | 35 |
| $M_{11}$ | 120/0.13 | 277 | 25 |

FIG. 10

TABLE II
AMPLIFIER II DEVICE SIZES AND OPERATING POINTS

| Devices | W/L ($\mu m/\mu m$) | $I_D$ (nA) | $g_m/I_D$ ($V^{-1}$) |
|---|---|---|---|
| $M_{1a}$-$M_{1b}$ | 152/0.18 | 510 | 27 |
| $M_{2a}$-$M_{2b}$ | 12.8/20 | 255 | 20.7 |
| $M_{3a}$-$M_{3b}$ | 12.8/20 | 255 | 20.7 |
| $M_{4a}$-$M_{4b}$ | 0.8/25 | 27 | 16.6 |
| $M_{5a}$-$M_{5b}$ | 16/12 | 67 | 22.9 |
| $M_6$ | 192/1 | 1020 | 27 |

FIG. 11

TABLE III
OP-AMP DEVICE SIZES AND OPERATING POINTS

| Devices | W/L ($\mu$m/$\mu$m) | $I_D$ (nA) | $g_m/I_D$ ($V^{-1}$) |
|---|---|---|---|
| $M_{1a}$–$M_{1b}$ | 100/0.18 | 80 | 29 |
| $M_{2a}$–$M_{2b}$ | 1/5 | 40 | 21 |
| $M_{3a}$–$M_{3b}$ | 1/5 | 40 | 21 |
| $M_{4a}$–$M_{4b}$ | 8/5 | 320 | 21 |
| $M_{5a}$–$M_{5b}$ | 32/4 | 320 | 21 |
| $M_6$ | 200/1 | 160 | 28 |

TABLE IV
COMPARISON AND PERFORMANCE SUMMARY OF AFEs

| | JSSC 2011 | JETCAS 2011 | TBCAS 2014 | JSSC 2015 |
|---|---|---|---|---|
| Power ($\mu W$)[r] | 2.44 | 56 | 23–46 | 1.4 |
| Supply (V) | 2.8 | 3.3 | +/−0.6 | 0.5 |
| Gain (dB) | 39.4 | 60 | Variable | 30 |
| Bandwidth (Hz) | 0.36–1.3k | 300 | 1–15 k | 1–500 |
| IRNoise ($\mu V_{RMS}$)[7] | 3.07 | 0.5 | 13[2] | 1.23 |
| NEF | 3.09 | 4.4 | 7 | 3.7 |
| PEF | 26.7[6] | 64[6] | 58.5[6] | 6.9 |
| PSRR (dB) | >80 | 69 | 39–93 | 67 |
| CMRR (dB) | >66 | 51 | 51–97 | 88 |
| Area (mm²) | 0.13 | 86[8] | 12.19[8] | 0.025 |
| %THD at mV$_{pp}$ Input | 1% (10) | 1% (2.6) | 1% (4.5)[4] | 0.4% (1) |
| Technology | 0.6 $\mu m$ | 0.35 $\mu m$ | 0.13 $\mu m$ | 65nm |

FIG. 20A

TABLE IV
COMPARISON AND PERFORMANCE SUMMARY OF AFEs

| | TBCAS 2016 | RHD2000 Intan | Amplifier I | Amplifier II |
|---|---|---|---|---|
| Power (μW)[†] | 1.08 | 7.4[9] | 0.216 | 0.69 |
| Supply (V) | 1 | 3.3 | 0.4 | 0.6 |
| Gain (dB) | 40 | 45.7 | 39 | 39[1] |
| Bandwidth (Hz) | 0.5–150 | 0.02–1k[10] | 12–190 | 2–175 |
| IRNoise (μV$_{RMS}$)[7] | N/A[3] | 2.4 | 2.19 | 2.3 |
| NEF | 4.52[5] | 4.37[9] | 4.65 | 7.22 |
| PEF | 20.43[5] | 63[9] | 11.7 | 31.3 |
| PSRR (dB) | 68 | 75 | 58 | 70 |
| CMRR (dB) | 82 | 82 | 60 | 74 |
| Area (mm²)[8] | 0.085 | N/A | 0.044 | 0.052 |
| %THD at mV$_{pp}$ Input | 1% (4) | 0.8% (10) | 1% (5) | <1%(0.2) |
| Technology | 65nm | N/A | 0.13μm | 0.18 μm |

[†]Power dissipation includes only the front-end amplifier unless otherwise stated. [1]58 dB for the whole AFE. [2] 7.3 μV$_{RMS}$ for 300Hz–15 kHz. [3] for 1–300 Hz μV$_{RMS}$. [3] 112 nV/√Hz at 150 Hz. [4] Including ADC. [5]Reported for a defined single frequency. Actual value is higher. [6]Value calculated from reported results. [7]Integrated over the bandwidth. [8] Total chip area. [9] Estimated over 1k Hz bandwidth. [10]Bandwidth tunable from 0.02–20kHz

FIG. 20B

IMPLANTABLE ELECTROCORTICOGRAM BRAIN-COMPUTER INTERFACE SYSTEM FOR RESTORING EXTREMITY MOVEMENT

CROSS REFERENCE

This application is a continuation-in-part and claims benefit of PCT Application No. PCT/US17/55652, filed Oct. 6, 2017, which claims priority to U.S. Provisional Patent Application No. 62/405,021, filed Oct. 6, 2016, the specification of which is incorporated herein in its entirety by reference.

GOVERNMENT SUPPORT

This invention was made with Government support under Grant No. CNS1446908 awarded by the National Science Foundation. The Government has certain rights in this invention.

FIELD OF THE INVENTION

The present invention relates to a biomedical technological device, more specifically, to a fully-implantable medical device for restoring brain-controlled movement of an extremity of a patient after a neural injury.

BACKGROUND OF THE INVENTION

Individuals with chronic spinal cord injury ("SCI") are almost universally affected by gait impairment or complete loss of gait function. These deficits have a profound negative impact on the independence and quality of life of those affected. In addition, excessive wheelchair reliance after SCI greatly increases the risk of medical complications, such as pressure ulcers, metabolic derangements, or life-threatening blood clots. The primary and secondary healthcare costs associated with SCI are estimated at $50 billion a year, presenting a significant public health concern. Currently, there are no biomedical solutions capable of restoring motor function after SCI. Therefore, clinically practical and socially acceptable solutions that can restore able-bodied-like gait function after SCI are desperately needed.

While promising, current electroencephalogram ("EEG") based brain-computer interfaces ("BCIs") have many limitations, such as the EEG's limited spatiotemporal resolution (~cm, ≤35 Hz and susceptibility to motion artifacts. These translate into erroneous BCI control, which, even if brief or infrequent, ray result in injury.

In addition, the EEG cap mounting/dismounting procedures are tedious and time consuming. Furthermore, the entire system (EEG cap, amplifiers, computer, and end-effector) is cumbersome and generally not viewed as aesthetically pleasing to potential users. While some progress has been recently made in EEG electrode technology, the above limitations remain largely unsolved. Hence, restoring walking with these EEG-based BCIs that is reliable, practical, and widely adopted by patients, their families, and physicians is unlikely.

The above problems may be addressed by utilizing electrocorticogram ("ECoG") signals, which are recorded invasively from the surface of the brain. Compared to EEG, ECoG signals have higher spatiotemporal resolution (~mm, ~200 Hz), a higher signal-to-noise ratio, and are immune to motion artifacts. In response to movements, ECoG signals exhibit a robust and predictable decrease in α (8-12 Hz) and β (13-30 Hz) band powers, and an increase in high γ (80-160 Hz) band power over the motor cortex, i.e., the brain areas that control movement. These in turn facilitate superior BCI performance, with accuracy as high as 100%. In addition, since ECoG electrode grids can be permanently implanted, there are no mounting/dismounting procedures and signals have been shown to remain stable >5 years. To exploit permanently implanted ECoG grids for BCI-controlled ambulation while making the system acceptable to potential users, a fully implanted cyber-physical system ("CPS") that can acquire and analyze ECoG signals to generate commands for a lower extremity prosthesis is detailed in the present invention.

Currently available BCI systems rely on intracortically implanted microelectrodes, which are not conducive to permanent implantation. For example, scar tissue formation and electrode dissolution significantly degrade signal quality over time, ultimately compromising the BCI performance. In addition, these systems rely on bulky, skull-protruding components for signal acquisition. Several groups have proposed to address these limitations by wireless data transmission. However, chronic brain exposure to high-frequency radiation may cause thermal injury and its oncogenicity remains a contentious topic. Finally, conventional BCI data analysis algorithms rely on high-performance processors that are not implantable due to size, heat dissipation, and power consumption constraints. Consequently, BCI operation has mostly been restricted to laboratory exercises. In summary, for BCI systems to be clinically viable and widely accepted, these limitations must be overcome.

Motivated by the shortcomings of existing BCIs, the present invention discloses a ground-breaking, fully implantable ECoG-based BCI system that is safe, has long-term signal stability, has no protruding components, and conforms to stringent human implantation constraints. As part of the present invention, the front-end of such a BCI system consists of an ECoG grid placed over the brain paracentral lobule (the brain area presumed to control gait).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

The present invention features a fully-implantable BCI system for acquiring and analyzing ECoG signals from a brain of a patient to enable direct brain control of a limb prosthetic. The plurality of electrodes may be implanted in a subdural space of the brain to allow a plurality of tissue layers, disposed between the plurality of electrodes and the cortical tissue, to act as insulation for the cortical tissue (from the plurality of electrodes). This subdural implantation circumvents the formation of scar tissue and dissolution of the electrodes (as is typically observed in intracortically implanted microelectrodes), thus providing ECoG signal stability, as penetration of the cortical tissue is avoided.

In some embodiments, the system comprises; a bioelectric signal acquisition system ("skull unit") fully implanted in the skull of the patient; a chest wall unit implanted within a chest wall of the patient; and a subcutaneous tunneling cable, operatively coupling the skull unit and the chest wall unit, comprising one or more wires. In further embodiments, the skull unit comprises an ECoG grid comprising the plurality of electrodes.

In an embodiment, an ultra low-power ("ULP") amplifier array is operatively coupled to the ECoG grid for amplifying the ECoG signals acquired. In another embodiment, a ULP serializer integrated circuit ("IC") is operatively coupled to the ULP amplifier array. As the skull unit employs ultra low-power components and operates as a battery-less system, power consumption within the skull unit is sufficiently low to prevent heating of local tissues.

In additional embodiments, the chest wall unit comprises: a low-power analog-to-digital converter ("ADC"); a low-power digital signal processor ("DSP") operatively coupled to the low-power ADC; a memory module, operatively coupled to the low-power DSP, storing a set of instructions; and a low-power radio frequency transceiver ("RF TRX") operatively coupled to the DSP. In some embodiments, a battery provides power to the low-power ADC, the low-power DSP, the memory module, and the low-power RF TRX. In other embodiments, the battery is wirelessly rechargeable. A wireless charging coil may be operatively coupled to the battery for wirelessly charging and recharging the battery.

In supplementary embodiments, the subcutaneous tunneling cable operatively couples the ULP integrated circuit ("IC") and the low-power ADC. In another embodiment, the subcutaneous tunneling cable also supplies power, from the battery, to the ULP serializer IC and the ULP amplifier array.

Consistent with previous embodiments, after amplification via the ULP amplifier array, the ECoG signals are serialized by the ULP serializer IC to produce a serialized data set. The tunneling cable may then route the serialized data set to the chest wall unit.

In some embodiments, the serialized data set is digitized by the low-power ADC and subsequently transmitted to the low-power DSP for de-serialization, digital re-timing, and processing, comprising the execution of the set of instructions stored by the memory module (107), resulting in a plurality of real-time commands. The plurality of real-time commands may be stored by the memory module and/or wirelessly transmitted to the limb prosthetic via the low-power RF TRX and executed by said prosthetic.

One of the unique and inventive technical features of the present invention is the implantation of the plurality of electrodes in the subdural space of the brain. As previously mentioned, intracortically implanted microelectrodes are subject to scar tissue formation and microelectrode dissolution, which significantly degrades the quality of the neural signal over time. In contrast, the subdural implantation disclosed in the present invention allows a plurality of tissue layers to be disposed between the cortical tissue and the plurality of electrodes (as shown in FIG. 14). This implantation technique results in a lack of formation of scar tissue and no dissolution of the electrodes, thus the quality of acquired ECoG signals is effectively maintained.

The subdural space was chosen as it provides both safety and longevity (i.e. it is safer and longer-lasting than intracortically implanted microelectrodes). FDA-approval of a reactive neurostimulator [11], which is used for seizure prevention, has demonstrated that ECOG electrodes may be safely implanted in the subdural space for >5 years. Further, it was found that their signals did not degrade significantly over this time period. This is not the case for the state-of-the-art intracortically implanted microelectrodes, whose signals degrade over time, and ultimately disappear due to gliosis, scar tissue formation, inflammatory processes, etc. Thus, an optimal signal quality and safety/longevity of microelectrodes is not optimally exploited in current state-of-the-art systems. Finally, subdurally implantable electrodes are FDA-cleared for clinical procedures such as epilepsy surgery evaluation and the aforementioned reactive neurostimulator.

Another unique and inventive technical feature of the present invention is the bi-partitioning of the skull unit and chest wall unit into two different locations when implanting the system into the body. Unlike invasive BCIs that utilize bulky recording hardware and rely on skull-protruding electronic components that emit wireless transmission from the brain, the present invention effectively reduces the size of the skull unit and relocates the source of wireless transmissions to the chest wall, which has a higher tolerance for the size and heat dissipation than the skull, thus reducing exposure of the skull bone marrow and the brain to potentially harmful RFs. Further still, the linking of the units by a subcutaneous tunneling cable eliminates the need for wireless data transmission between the skull unit and the chest wall unit. None of the presently known prior references or work has the unique inventive technical feature of the present invention.

BRIEF DESCRIPTION OF THE DRAWINGS

This patent application contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIG. 10 shows Table I: Amplifier I Device Sizes and Operating Points.

FIG. 11 shows Table II: Amplifier II Device Sizes and Operating Points.

19A shows the PSD of the BSA II and commercial bioamplifier from 30 seconds of ECoG data.

Figure 19A:
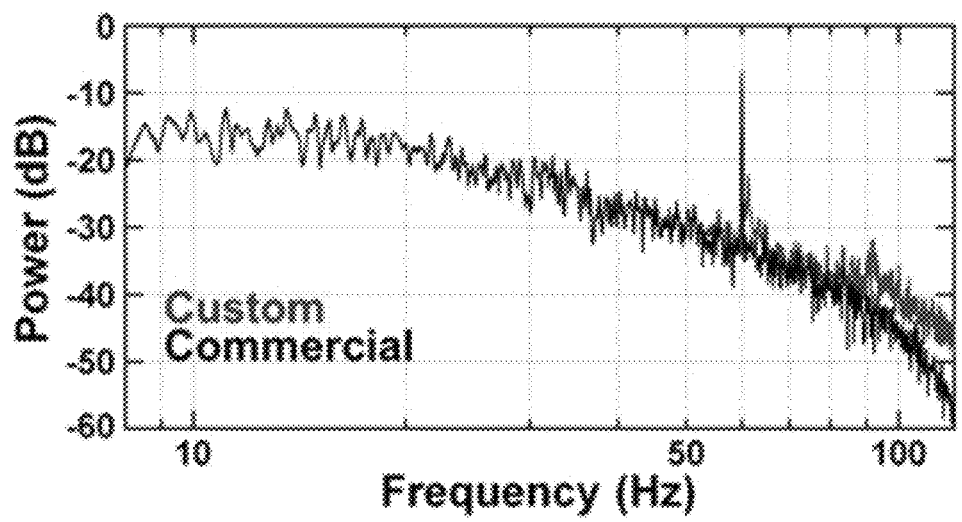
Figure 19B:
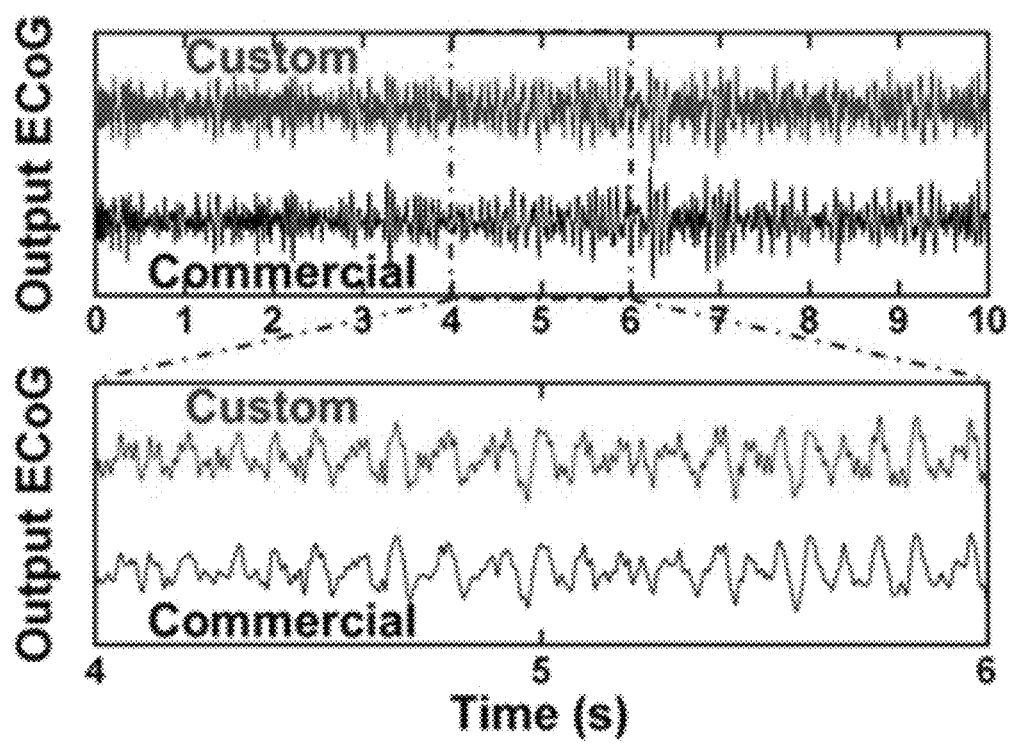

FIG. 19B shows the filtered (8-120 Hz) time-series data from the implanted ECoG grid with the BSA II and commercial bioamplifier (top) and a zoomed-in view of the recorded ECoG (bottom).

FIGS. 20A-20B show Table IV: A Comparison and Performance Summary of analog front ends ("AFEs").

Figure 21:
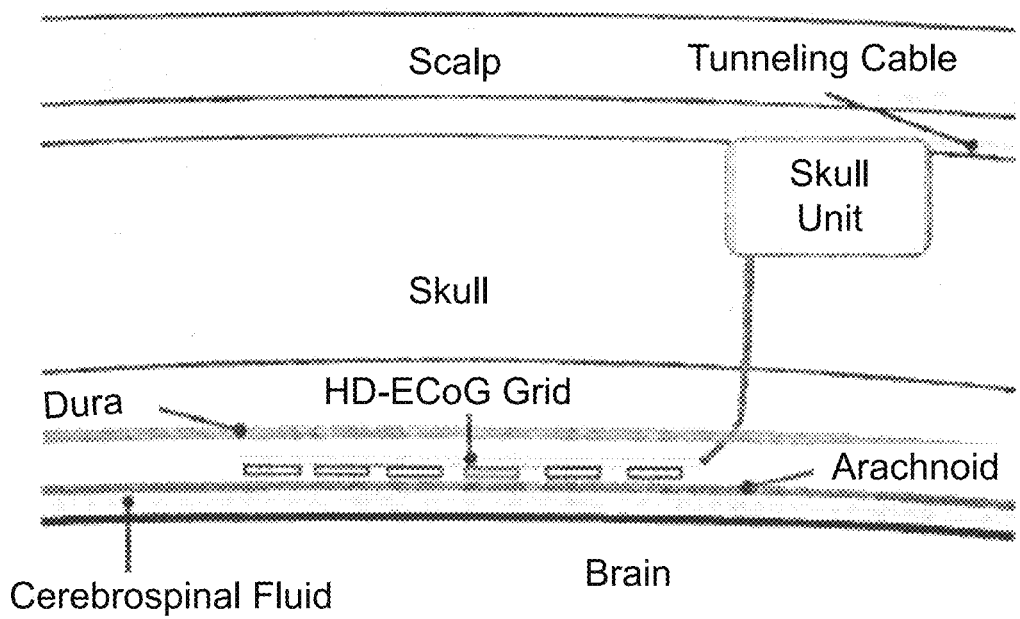

FIG. 21 shows a cross-sectional view of the skull unit and ECoG grid placement.

Figure 22:
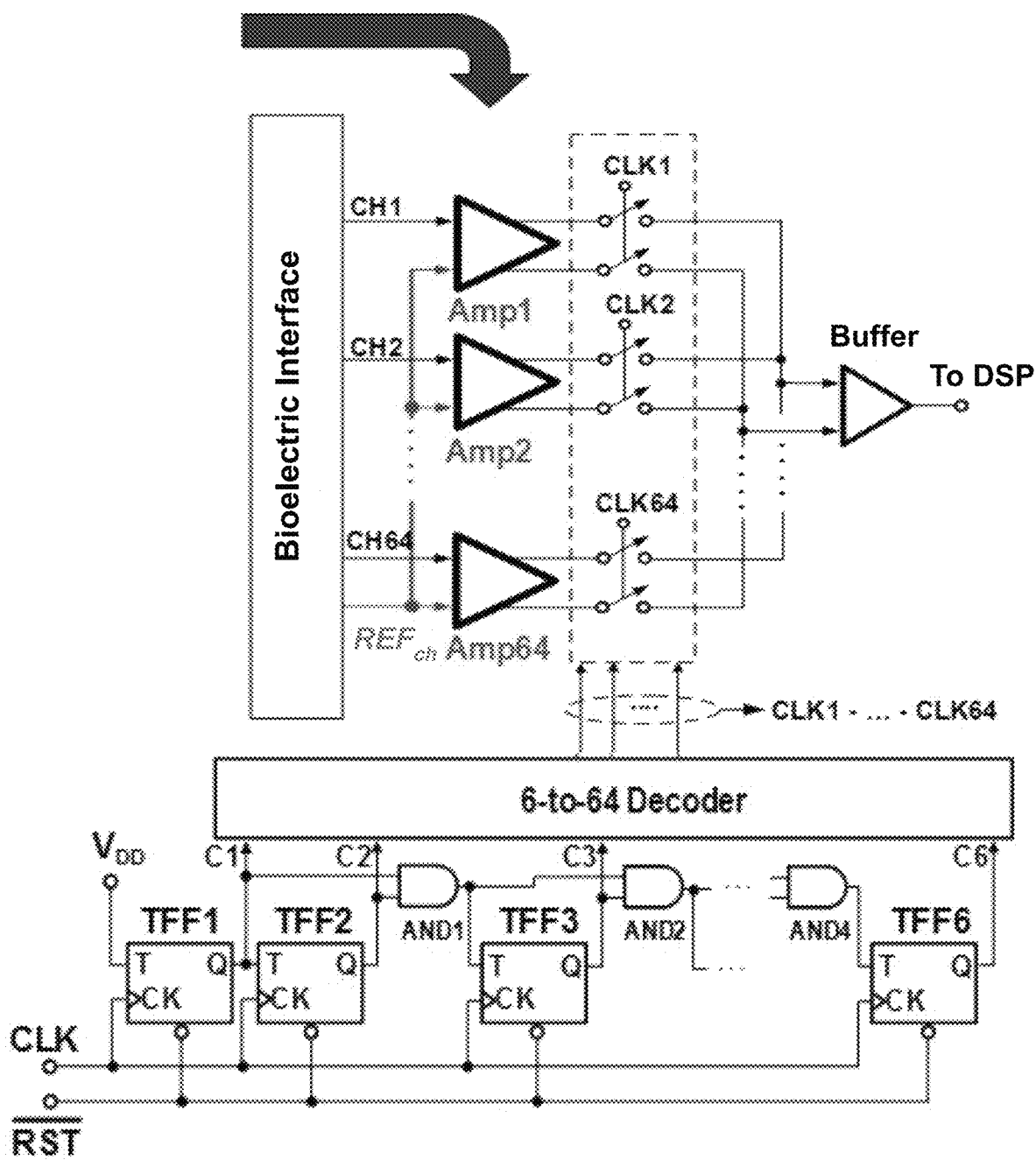

FIG. 22 shows a system-level block diagram of the skull unit, biased in the weak inversion ("WI") region, comprising an array of 64 fully differential amplifiers and a serializer, which is controlled by an on-chip synchronous counter-based control circuitry.

Figure 23:
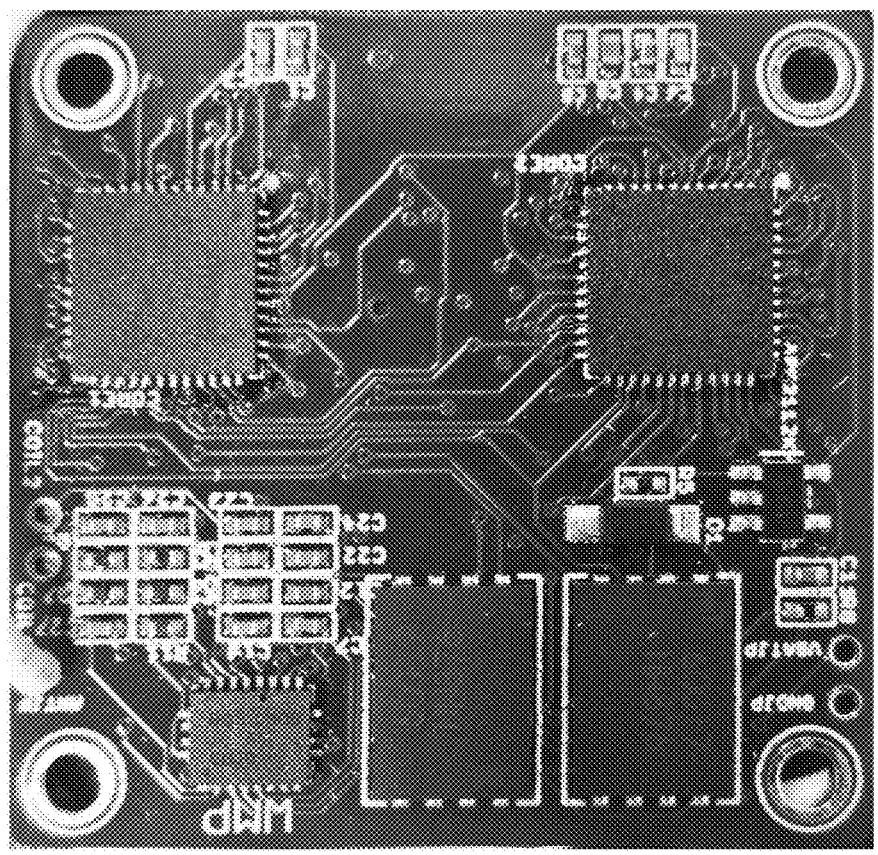

FIG. 23 shows a photograph of the fabricated chest wall unit circuit board.

Figure 24:
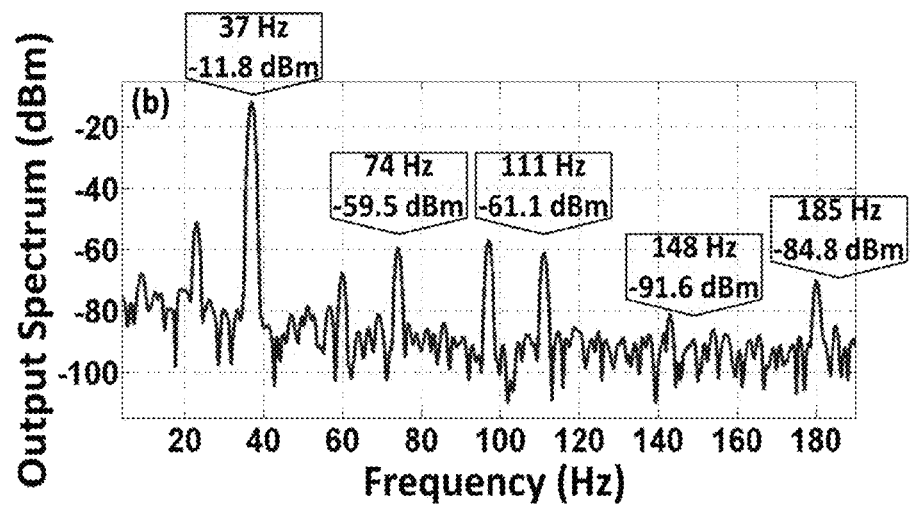

FIG. 24 shows the measured and simulated gain and noise responses for a single channel of BSA II.

Figure 25A:
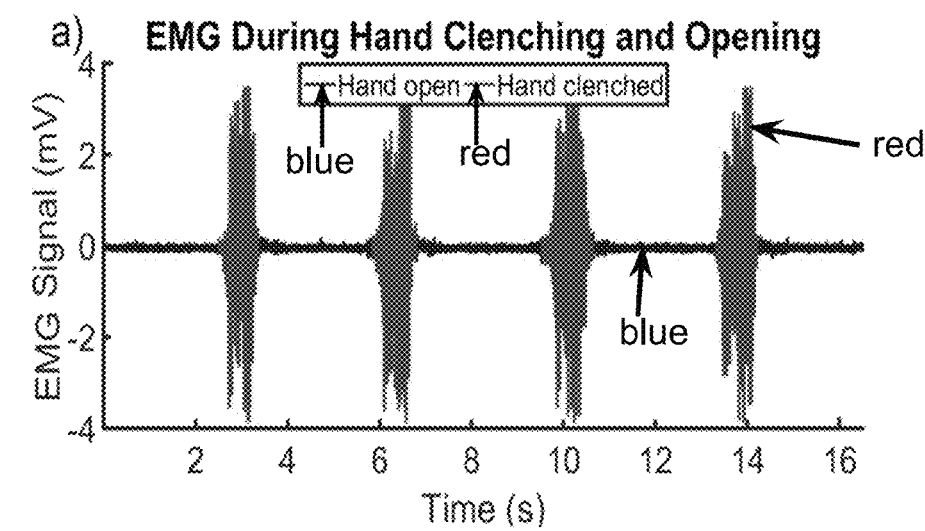

FIG. 25A shows an electromyography ("EMG") times series during hand-clenched and hand-open states, where a ~30 dB broadband increase in amplitude during the hand-clenched state is seen.

Figure 25B:
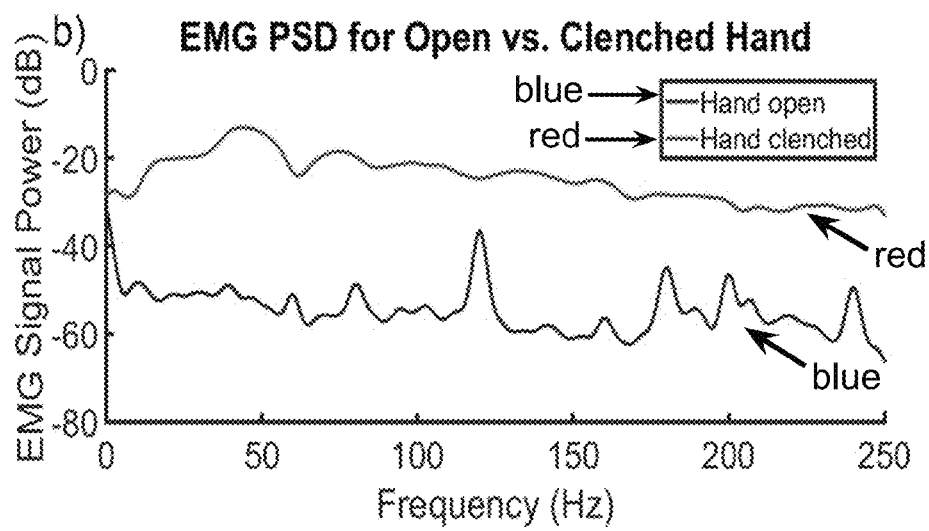

FIG. 25B shows the power spectral density ("PSD") during hand-clenched and hand-open states.

Figure 26:
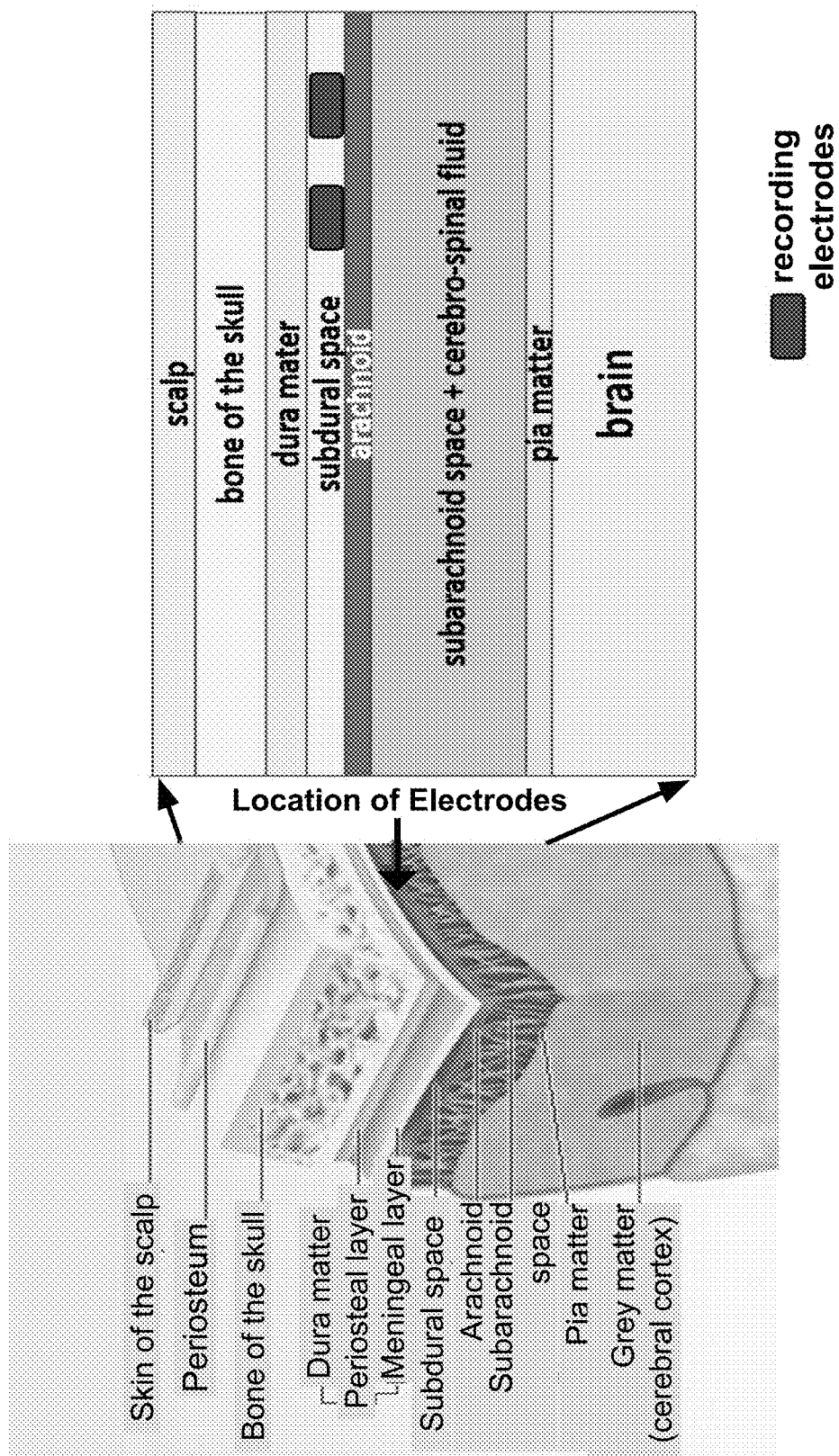

FIG. 26 shows a preferred placement of the plurality of electrodes in the subdural space of the brain.

DETAILED DESCRIPTION OF THE INVENTION

Referring now to FIGS. 1-26, the present invention features a fully-implantable BCI system for acquiring and analyzing ECoG signals from a brain of a patient to enable direct brain control of a limb prosthetic (e.g., a robotic gait exoskeleton ("RGE") or a functional electrical stimulation ("FES") system). In an embodiment, the limb prosthetic is attached to an upper or lower extremity of the patient to enable movement of said extremity. In another embodiment, the RGE or FES is attached to an arm(s) or leg(s) of the patient.

As is well understood by one of ordinary skill in the art, an intracortically implanted microelectrode is subject to the formation of scar tissue (surrounding the intracortically implanted microelectrode) and an eventual dissolution of said microelectrode, which ultimately results in a degradation of the acquired ECoG signals. Therefore, in an exemplary embodiment of the present invention, the plurality of electrodes is implanted in a subdural space of the brain to acquire the EcoG signals. This allows a plurality of tissue layers (e.g., arachnoid, subarachnoid space, and pia matter) to separate the plurality of electrodes from the cortical tissue, thus effectively insulating the cortical tissue. The subdural implantation circumvents the formation of scar tissue and the dissolution of electrodes, thus providing ECoG signal stability.

In some embodiments, the system comprises: a skull unit (102) configured to be fully implanted in the skull of the patient; a chest wall unit (101) implanted within a chest wall of the patient; and a subcutaneous tunneling cable (110) operatively coupling the skull unit (102) and the chest wall unit (101). In further embodiments, the skull unit (102) comprises an ECoG grid (104) comprising the plurally of electrodes.

In an embodiment, a ULP amplifier array (106) is operatively coupled to the ECoG grid (104) for amplifying the ECoG signals acquired. In another embodiment, a ULP serializer IC (108) is operatively coupled to the ULP amplifier array (106). As the skull unit (102) employs ULP components and operates as a battery-less system, power dissipation within the skull unit (102) is sufficiently low to prevent heating of local tissues (e.g., brain, skull, and scalp tissues). As will be subsequently discussed, experimental results estimate said power dissipation to be below 50 µW, falling well within biomedical constraints for safe heat dissipation. Further, experimental results estimated the power dissipation of the ULP amplifier array (106) to be about 0.216 µW for a first embodiment (Amplifier I) and about 0.69 µW for a second embodiment (Amplifier II). An experimental estimate of the power dissipation of the ULP serializer IC (108) was negligible (i.e., within a nW range).

In additional embodiments, the chest wall unit (101) comprises: a low-power ADC (103); a low-power DSP (105) operatively coupled to the low-power ADC (103); a memory module (107), operatively coupled to the low-power DSP (105), storing a set of instructions; and a low-power RF TRX (109) operatively coupled to the DSP (105). In an alternate embodiment, the low-power ADC (103) is disposed in the skull unit (102), operatively coupled between the ULP serializer IC (108) and the subcutaneous tunneling cable (110). Experimental results estimate the power consumption of the low-power ADC (103) to be below 50 µW. Moreover, experimental results estimate the power consumption of each processor core of the low-power DSP (105) to be about 7-10 mA at 3.3 V and the power consumption of the low-power RE TRX (109) to be about 2.8 mW.

In some embodiments, a battery (111) provides power to the low-power ADC (103), the low-power DSP (105), the memory module (107), and the low-power RE TRX (109). In other embodiments, the battery is wirelessly rechargeable.

In an embodiment, the battery (111) is a lithium iodide battery. A wireless charging coil (113) may be operatively coupled to the battery (111) for wirelessly charging and recharging the battery (111).

In supplementary embodiments, the subcutaneous tunneling cable (110) operatively couples the ULP serializer IC (108) of the skull unit (102) and the low-power ADC (103) of the chest wall unit (101). In another embodiment, the subcutaneous tunneling cable (110) also supplies power, from the battery (111), to the ULP serializer IC (108) and the ULP amplifier array (106).

Consistent with previous embodiments, after amplification via the ULP amplifier array (106), the ECoG signals are serialized by the ULP serializer IC (108) to produce a serialized data set. The tunneling cable (110) may then route the serialized data set to the chest wall unit (101). As the ECoG signals are serialized prior to transmission to the chest wall unit (101), a number of wires comprising the tunneling cable (110) are effectively reduced to at least one, thus reducing power requirements. As a non-limiting example, since the ECoG signals are measured at multiple spatial locations in the brain, 64 electrodes organized into an 8×8 array is typically required. It would be unsafe and impractical to route a tunneling cable comprising 64 wires subcutaneously from the skull (e.g., through the neck) to the chest wall unit (101). Therefore, serialization of the 64 (or even more) ECoG signals into a single signal would reduce the number of required wires from 64 to 1.

In some embodiments, the serialized data set is digitized by the low-power ADC (103) and subsequently transmitted to the low-power DSP (105) for de-serialization and digital re-timing to produce a data set for processing. The data set may be processed via the low-power DSP (105) or via an external computer. In an embodiment, processing the data set via the low-power DSP (105) comprises an execution of the set of instructions stored by the memory module (107), resulting in a plurality of real-time commands. Said commands may be stored by the memory module (107) and/or wirelessly transmitted to the prosthetic via the low-power RF TRX (109), where the prosthetic executes the commands and performs tasks associated with the commands.

In other embodiments, the set of instructions executed by the low-power DSP (105) comprises one or more BCI algorithms. These algorithms process the acquired ECoG signals to generate the plurality of real-time commands, which provide direction for the movement of the prosthetic. "Electrocorticographic Encoding of Human Gait in the Leg Primary Motor Cortex," McCrimmon, et al. provides a non-limiting example of such an algorithm for directing the movement of a patient's legs disposed in a human gait exoskeleton. For instance, since the brain motor cortex modulates the ECoG high-gamma band to initiate and stop walking and to control the rate of walking, a decoding algorithm may utilize this physiological feature to determine when the user intends to walk or not walk, and at what walking speed. Thus, in some embodiments, the present invention may be used to determine when the patient intends to walk and at what speed.

In one embodiment, the low-power RF TRX (109) is dual mode, where a first mode is a high data rate transmission mode (>1 Mbit/s) and a second mode is a low data rate (~1 Kbit/s) transmission mode. The plurality of real-time commands may be wirelessly transmitted to the prosthetic via the low-power RF TRX (109) operating in the second mode.

In an alternate embodiment, the data set is transmitted to the external computer via the low-power RF TRX (109). In some embodiments, the low-power RF TRX (109) transmits the data set to the external computer while operating in the first mode. In one embodiment, the external computer processes the data set via one or more decoding models generated by the one or more BCI algorithms to generate the plurality of real-time commands, which may then be transmitted to the prosthetic for execution. Nonlimiting examples of these decoding models are detailed in C. E. King, P. T. Wang, C. M. McCrimmon, C. C. Y. Chou, A. H. Do, and Z. Nenadic, *J. NeuroEng. Rehabil.*, vol. 12(80), 2015[11]; A. H. Do, P. T. Wang, G. E. King, S. N, Chun, and Z, Nenadic, *J. NeuroEng. Rehabil.*, vol. 10(111), 2013[12]; C. E. King, P. T. Wang, L. A. Chui, A. H. Do, and Z. Nenadic, *J. NeuroEng. Rehabil.*, vol. 10(77), 2013[13]; P. T. Wang, C. E. King, L. A. Chui, A. H. Do, and Z. Nenadic, *J. Neural Eng.*, vol. 9(5), pp. 056016, 2012[14]; and P. T. Wang, E. J. Puttock, C. E. King, A. Schombs, J. J. Lin, M. Sazgar, F. P. K. Hsu, S. J. Shaw, D. E. Millett, C. Y. Liu, L. A. Chui, A. H. Do, and Z. Nenadic, in *Proc of the 6th Annual international IEEE EMBS Conference on Neural Engineering*, pp. g69-972, 2013[15].

The present invention additionally features a method for enabling direct brain control of a prosthetic of a patient. The method may comprise providing a brain-computer interface system. In exemplary embodiments, said system comprises: a bioelectric signal acquisition system (102), referred to herein as a skull unit, a chest wall unit (101), and a subcutaneous tunneling cable (110).

In some embodiments, the skull unit comprises an electrocorticogram ("ECoG") grid (104) comprising a plurality of electrodes configured to acquire ECoG signals from a brain of the patient, an ultra low-power ("ULR") amplifier array (106), operatively coupled to the ECoG grid (104), and a ULP serializer integrated circuit ("IC") (108) operatively coupled to the ULP amplifier array (106). In other embodiments, the chest wall unit (101) comprises a low-power analog-to-digital converter ("ADC") (103), a low-power digital signal processor ("DSP") (105) operatively coupled to the low-power ADC (103), a memory module (107) operatively coupled to the low-power DSP (105) storing a set of instructions, a low-power radio frequency transceiver ("RF TRX") (109) operatively coupled to the low-power DSP (105), and a wirelessly rechargeable battery (111) providing power to the low-power ADC (103), the low-power DSP (105), the memory module (107), and the low-power RF TRX (109). In additional embodiments, the subcutaneous tunneling cable (110) operatively couples the ULP serializer IC (108) of the skull unit (102) to the low-power ADC (103) of the chest wall unit (101). In an embodiment, said tunneling cable (110) also provides power from the battery (111) to the ULP serializer IC (108) and the ULP amplifier array (106).

Consistent with previous embodiments, the present method may further comprise fully implanting the brain-computer interface system into the patient, where the skull unit is implanted into a skull of the patient such that the plurality of electrodes is implanted in a subdural space of the brain, and where the chest wall unit (101) is implanted into a chest wall of the patient; acquiring said ECoG signals via the plurality of electrodes; amplifying the ECoG signals acquired via the ULP amplifier array (108); serializing the ECoG signals via the ULP serializer IC (108) to produce a serialized data set, routing the serialized data set to the low-power ADC (103) of the chest wall unit (101) via the tunneling cable (110), digitizing the serialized data set via the low-power ADC (103); and transmitting the serialized data, after digitization, to the low-power DSP (105) for de-serialization and digital re-timing to produce a data set for processing.

In some embodiments, the data set is processed via the low power DSP (105), or via an external computer, to produce a plurality of real-time commands. The prosthetic may execute said commands and performs tasks associated with said commands. In one embodiment, the tunneling cable (110) routes the serialized data set from the skull unit (102), through a neck of the patient, to the chest wall unit (101). Further, as the ECoG signals are serialized prior to transmission to the chest wall unit (101), a number of wires comprising the tunneling cable (110) is effectively reduced to at least one.

In an alternate embodiment, the low-power ADC (103) is disposed in the skull unit (102), operatively coupled between the ULP serializer IC (108) and the subcutaneous tunneling cable (110).

In one embodiment, the ULP amplifier array (106) is a 64-channel ULP amplifier array.

In another embodiment, the low-power DSP (105) has an adaptive power management unit for placing components of the chest wall unit (including itself) into sleep mode when not in use.

In some embodiments, the battery (111) is a lithium iodide battery. A wireless charging coil (113) may be operatively coupled to the battery for wirelessly charging and recharging the battery (111).

In other embodiments, the low-power RF TRX (109) is dual mode, where a first mode is a high data rate transmission mode and a second mode is a low data rate transmission mode. Processing the data set via the low-power DSP may comprise an execution of the set of instructions, resulting in the plurality of real-time commands. Said commands may be wirelessly transmitted to the prosthetic via the low-power RF TRX (109) operating in the second mode. Alternately, the data set may be transmitted to the external computer for processing via the low-power RF TRX (109) operating in the first mode. In additional embodiments, the external computer processes the data set via one or more decoding models generated by the one or more BCI algorithms to generate the plurality of real-time commands, which are transmitted to the prosthetic for execution. Nonlimiting examples of these decoding models are detailed in C. E. King, P. T. Wang, C. M. McCrimmon, C. C. Y. Chou, A. H. Do, and Z. Nenadic, *J. NeuroEng. Rehabil.*, vol. 12(80), 2015[11]; A. H. Do, P. T. Wang, C. E. King, S. N. Chun, and Z. Nenadic, *J. NeuroEng. Rehabil.*, vol. 10(111), 2013[12]; C. E. King, P. T. Wang, L. A. Chui, A. H. Do, and Z. Nenadic, *J. NeuroEng. Rehabil.*, vol. 10(77), 2013[13]; P. T. Wang, C. E. King, L. A. Chui, A. H. Do, and Z. Nenadic, *J. Neural Eng., vol.* 9(5), pp. 056016, 2012[14]; and P. T. Wang, E. J. Puttock, C. E. King, A. Schombs, J. J. Lin, M. Sazgar, F. P. K. Hsu, S. J. Shaw, D. E. Millett, C. Y. Liu, L. A. Chui, A. H. Do, and Z. Nenadic, *Proc. of the 6th Annual International IEEE EMBS Conference on Neural Engineering*, pp. 969-972, 2013[15].

In supplementary embodiments, the prosthetic is attached to a lower extremity of the patient to enable movement of said extremity. In some embodiments, the prosthetic is a robotic gait exoskeleton ("RGE").

Experimental Details/Invention Specifications

Weak electrophysiological signals (e.g., the ECoG signals) must be amplified close to the site of acquisition (otherwise they would fade); but processed sufficiently far from the brain to avoid harmful heating of the brain, scalp, and skull tissue by processing elements (e.g., the low-power DSP (105) and supporting circuitry) as these elements draw significant power to effectively execute the complex BCI algorithms. This power requirement leads to a size and power consumption that preclude the processing elements' implantation in the skull. Thus, the DSP and supporting circuitry are implanted in the chest wall, which has a higher tolerance for the necessary size and heat dissipation than the skull.

To avoid wireless data transmission of the ECoG signals to the skull unit (102) and the chest wall unit (102), which would expose the brain, skull, and scalp tissue to potentially harmful radio frequencies ("RFs"), the skull unit (102) and the chest wall unit (102) are linked by the tunneling cable (110). Further, to reduce the physical footprint of the tunneling cable (110), the number of wires housed by the tunneling cable (110) are minimized by employing signal serialization (multiplexing) via the low-power ULP serializer IC (108).

As a non-limiting example, the ULP amplifier array (106) may be realized by a complementary metal-oxide-semiconductor ("CMOS") process, although other process technologies may be utilized. In some embodiments, a 64-channel ULP amplifier array (106) is employed. In other embodiments, the 64-channel ULP amplifier array (106) is a μW array with a 15-20 dB gain. Further, the ULP serializer IC (108) may be realized via a ULP 64+1 clocked binary-tree serializer. These components may be fabricated in a nanoscale CMOS process or silicon or beyond-silicon processes. Maximum performance and low power consumption have been demonstrated when the ULP amplifier array (106) employs transistors biased in the weak inversion ("WI") region of operation. In addition, a binary tree serializer is utilized in favor of its decoder-based counterpart for improved power efficiency.

The skull unit (102) may be constructed from a titanium alloy (the most commonly used biocompatible implant material) cylindrical enclosure with estimated dimensions of 1.5 cm diameter and 0.4 cm height. Based on preliminary simulations of the ULP amplifier array (106) and the ULP serializer IC (108) in a 65 nm CMOS process, the power consumption of the skull unit (102) was estimated to below 50 μW, falling well within a safe heat dissipation limit. The low-power ADC (103) operated with a maximum resolution and sampling rate of 16 bits and up to 2000 samples/sec/channel, respectively.

In exemplary embodiments, the features of the chest wall unit include: two microcontroller cores (48 Mhz each), 8 Gbit solid state storage, 2 Mbit RAM, wireless recharging capability, and a wireless transceiver (selectable from 400-470 Mhz). The chest wall unit may operate at 3.3 V, and draw approximately 30 mA current. In some embodiments, the chest wall unit may be approximately 3 cm×cm×1.5 mm in size. In other embodiments, the chest wall unit may be packaged into an ellipsoidal, titanium alloy enclosure, about 5 cm×4 cm×1 cm, which is comparable to pacemaker and deep brain stimulator implants. The chest wall unit may include a socket to accept the terminal of the tunneling cable (110).

System Architecture

Figure 1:
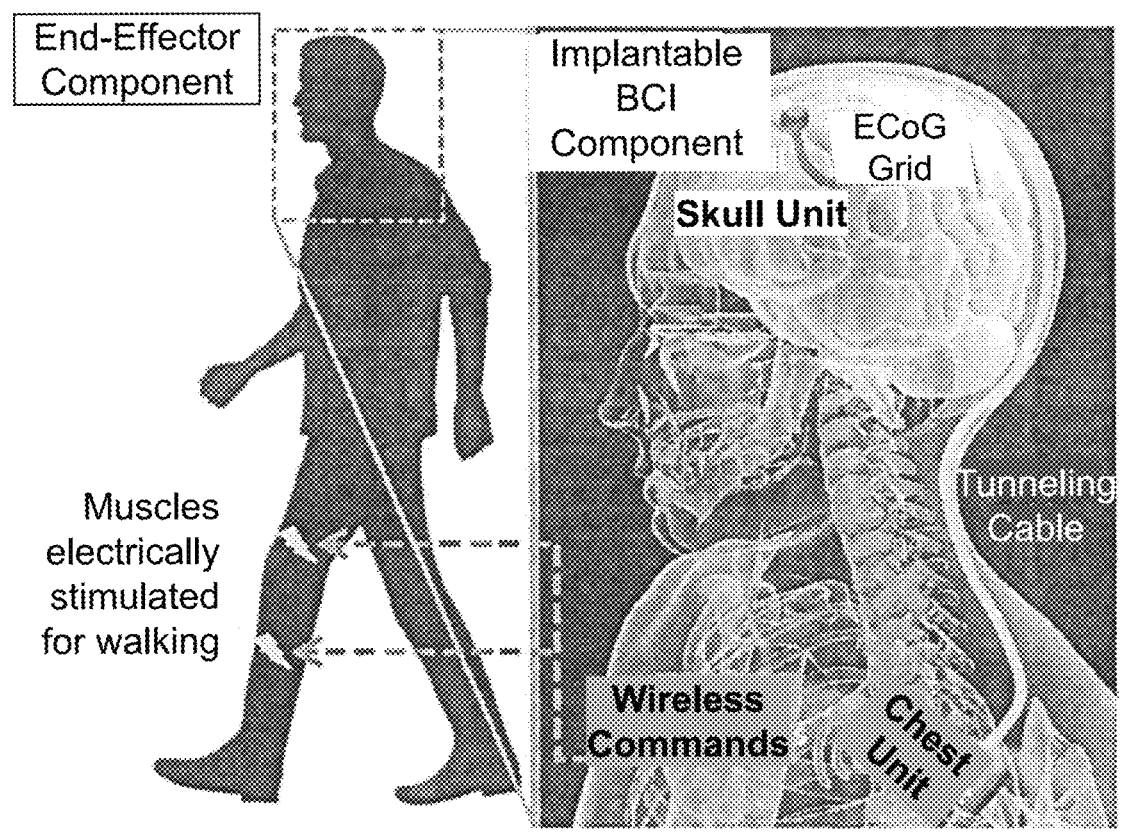
FIG. 1 shows an overview of the BCI system for permanent human implantation.
Figure 2A:
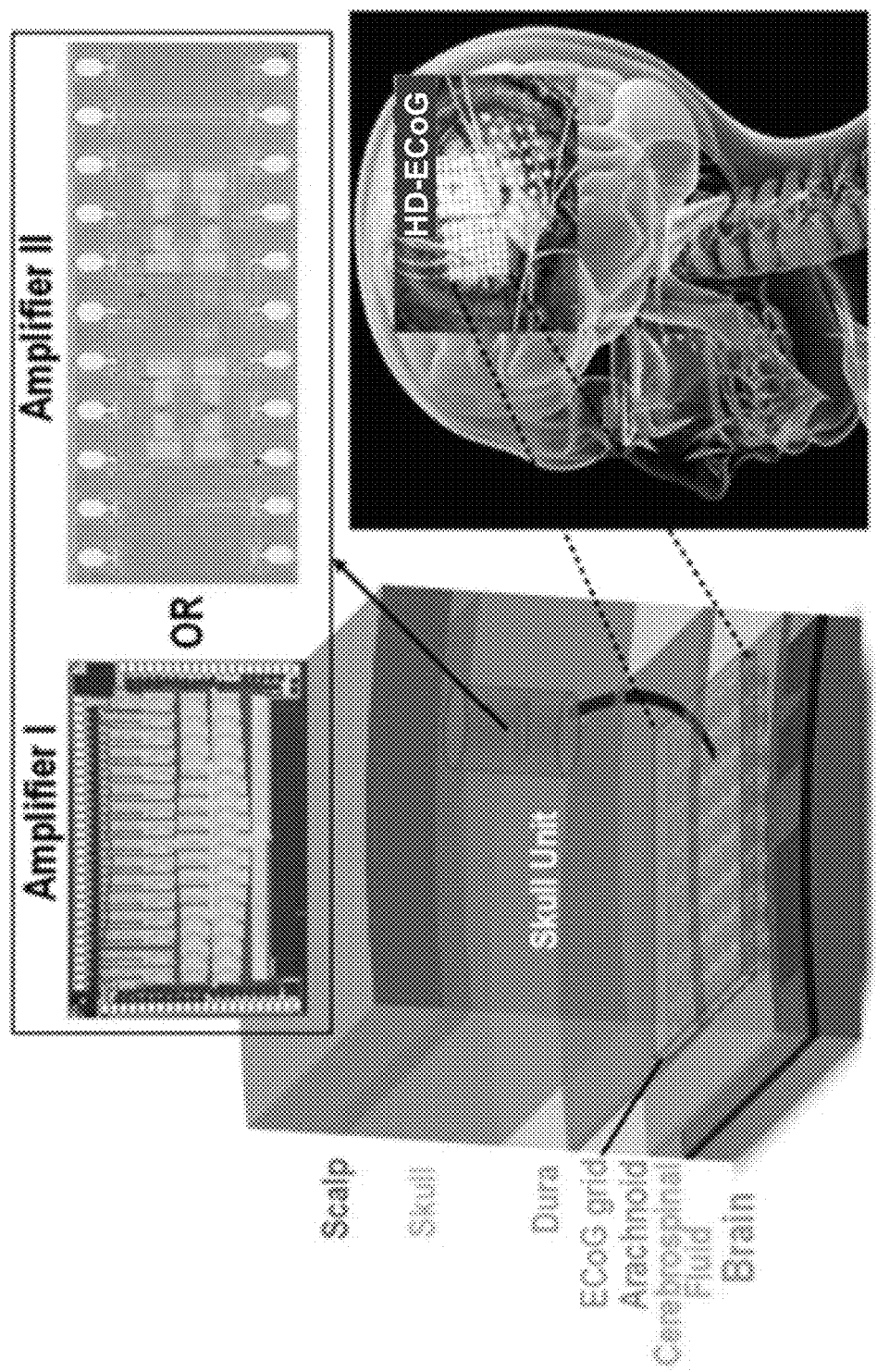
FIG. 2A shows a cross-sectional view of the envisioned fully implantable Brain Signal Acquisition ("BSA") circuit, enclosed within a skull unit module.
Figure 2B:
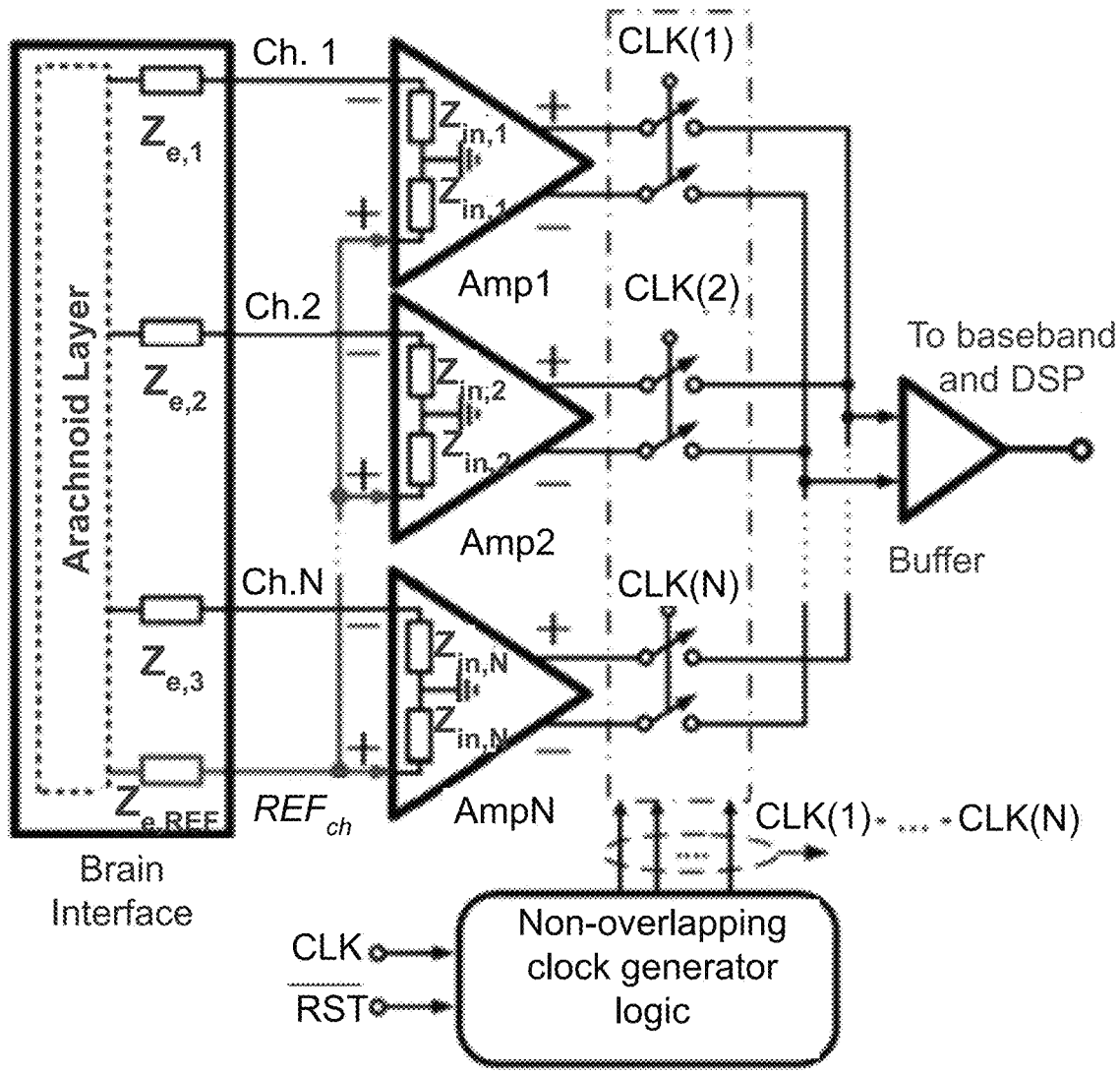
FIG. 2B shows a block diagram of the structure showing the brain interface electrodes with their corresponding impedances and BSA comprised of an array of fully differential amplifiers, serializer, and buffer.
Figure 2C:
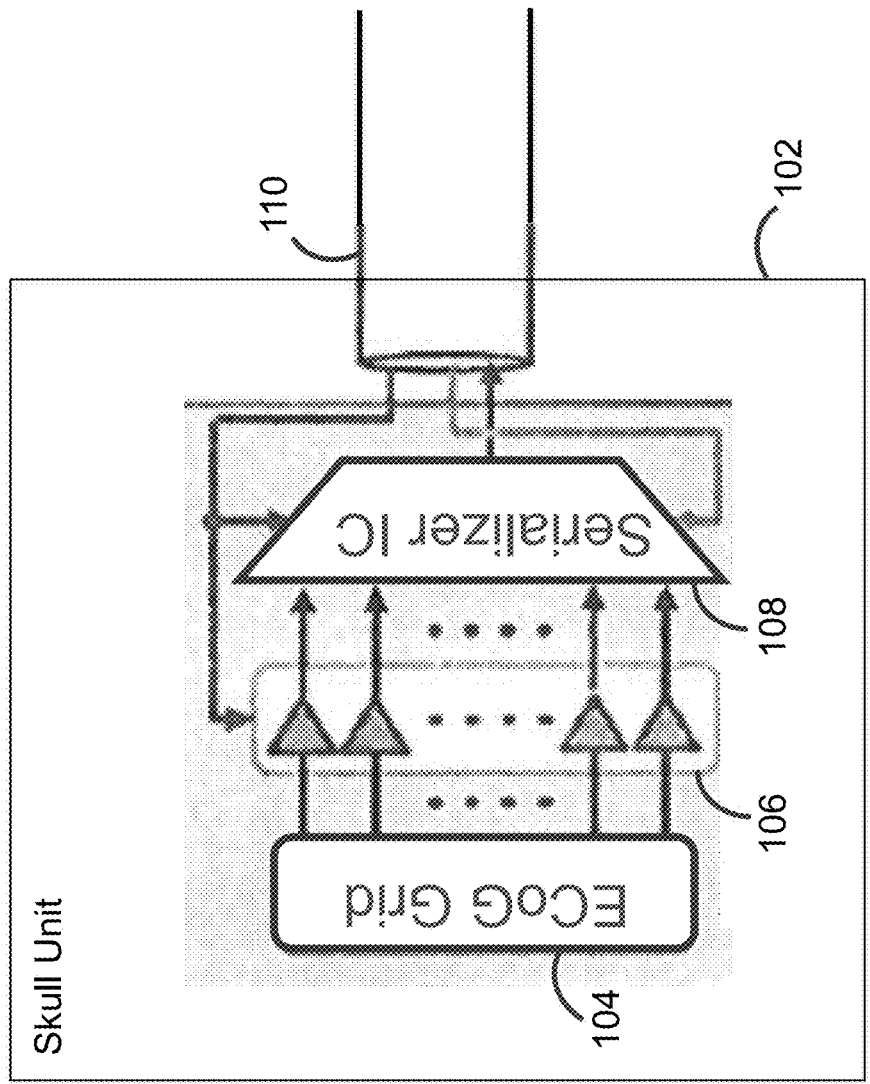
FIGS. 2C-2D show a block diagram of the BCI system of the present invention comprising a skull unit and chest wall unit connected by a subcutaneous channeling cable.
Figure 2D:
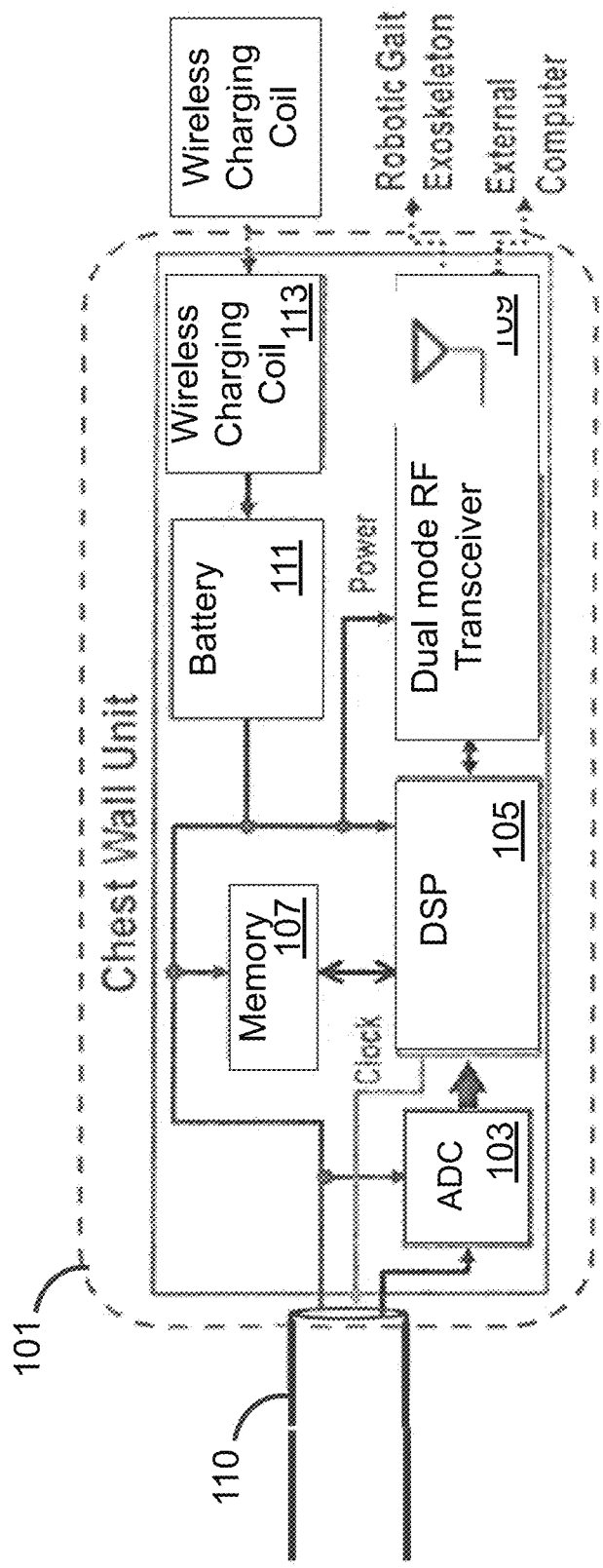

Responsible for sensing and amplification of microvolt-level brain signals, the amplifier array IC is a critical building block of a BSA front-end. To be employed as a fully implantable device, the signal acquisition front-end should be small in size and consume micro-watt levels of power. The system-level diagram of the proposed analog ("AFE") is shown in FIG. 2B. The AFE IC includes fully differential amplifiers, a serializer, and an output buffer all biased in the WI region. The outputs of the array are multiplexed in time to better facilitate input-output cable management by reducing the number of wires. The non-overlapping clock generator within the serializer generates N-phase clock signals, each with a 1/N duty cycle. Non-overlapping clock signals ensure that only one amplifier is connected to the output buffer at a time during the channel switchover. This work presents two ULP BSA front-ends: BSA I and BSA II. BSA I provides symmetrical and complementary signal amplification paths to achieve energy-efficient low noise signal conditioning. BSA II is designed to achieve a high common-mode rejection ratio ("CMRR") (i.e., better than 70 dB), thereby reducing the detrimental effect of power-line 60 Hz interference on the recorded signal.

Minimizing both noise and power dissipation imposes stringent design trade-offs in an AFE for an implantable system, mandating meticulous considerations at every level of the design process. For example, at the device level, this notion implies that transistors should be designed to operate in a region that yields minimum power consumption for a given infrared ("IR") Noise imposed by minimum detectable ECoG signal power.

Figure 3A:
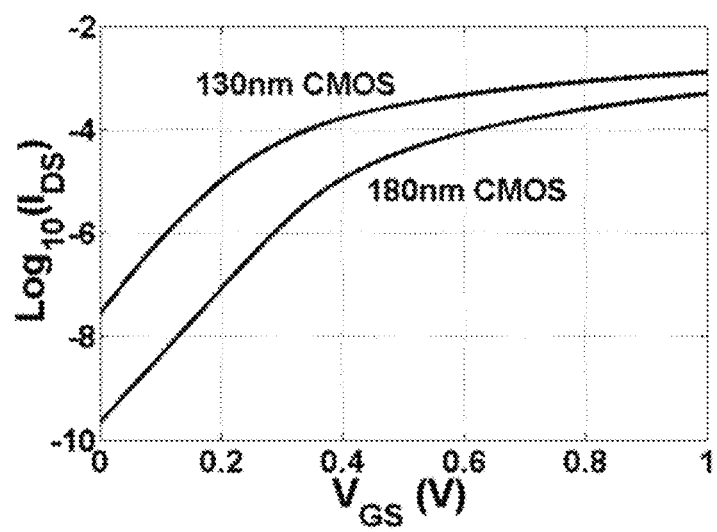
FIG. 3A shows the drain-source current, IDS, vs. gate-source, VGS, for the two technologies.
Figure 3B:
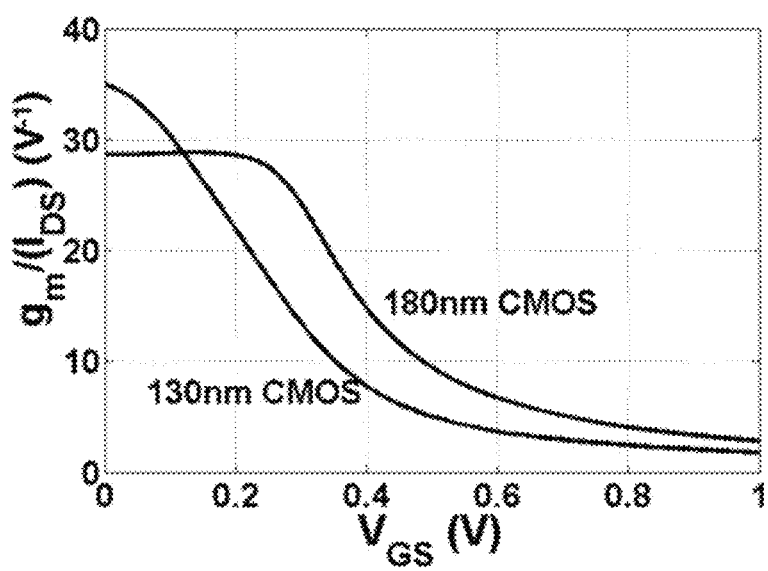
FIG. 3B shows the gm/IDS vs. VGS for the two technologies.

It is well-known that the metal-oxide semiconductor ("MOS") transistors in the WI region achieve a maximum gm/IDS ratio, resulting in the highest power efficiency at the cost of lower operation maximum bandwidth. FIGS. 3A-3B demonstrate gm/IDS and log 10(IDS) variations with respect to VGS for the two technologies given the same transistor sizes and bias conditions. Referring to FIG. 3A, a higher subthreshold leakage current and a higher slope are observed in the WI region for the 130 nm process compared to the 180 nm process, A higher slope corresponds to a larger gm for the same bias current. This feature translates to a better power efficiency (FIG. 3B) and noise performance for transistors designed in this specific 130 nm process. It is noteworthy that the gm/IDS plot for the 130 nm CMOS process does not show the expected flat region in the deep subthreshold region. This is because the BSIM4 device model was adopted for this process by the foundry. On the other hand, the 180 nm process employed the PSP device model, which can predict the 225 device behavior in deep subthreshold region more accurately.

ECoG signals typically have an amplitude of around 50-100 µV, with β and high-γ bands typically providing the most informative features for BCI applications. The IR Noise of the AFE should be kept lower than the noise floor of the ECoG electrodes. Recorded measurements using commercial BCI signal acquisition equipment showed that the RMS noise floor, integrated over a frequency range of 8-200 Hz, is typically less than 10 $\mu V_{RMS}$, which is in compliance with the data reported in literature. Low noise operation is of particular interest for high-γ band, because the ECoG signal power becomes weaker with frequency.

The CMRR and power-supply rejection ratios ("PSRR") should be large to attenuate the effect of environmental noise sources (e.g., 60 Hz power-line noise). Assuming an IR Noise level of 2 $\mu V_{RMS}$ in the presence of common-mode interference with 10 $mV_{RMS}$, a nominal 34 dB attenuation (i.e., 74 dB CMRR) is needed so that the output noise and interference voltage magnitudes are equal. In addition, the amplifier should show a high input impedance to lower the effect of common-mode interference. This attribute is especially important for multi-channel recordings since the impedance mismatch between electrodes ($Z_{e,1}, \ldots, Z_e, N$) as well as the mismatch between the impedance seen from the common reference input (parallel combination of $Z_{in,1}, \ldots, Z_{in,N}$ in FIG. 2B) and $Z_{in,k}$ (1≤k≤N) reduces the overall CMRR. Subdural electrodes' impedance has been reported (as well as measured) to be about 1 kΩ, thus the input impedance at the frequency of interest should be >1 MΩ. Moreover, large DC offsets associated with neural recording electrodes should be eliminated to minimize distortion or avoid saturation of the amplifier. Furthermore, electrical shielding and DC isolation are needed between the IC and implanted electrodes. Finally, the crosstalk in a multi-channel system should be mitigated to avoid contamination of the overall information recorded from different channels.

BSA 1: AN Array of 64 Amplifier 1 Circuits and a Serializer

Figure 4:
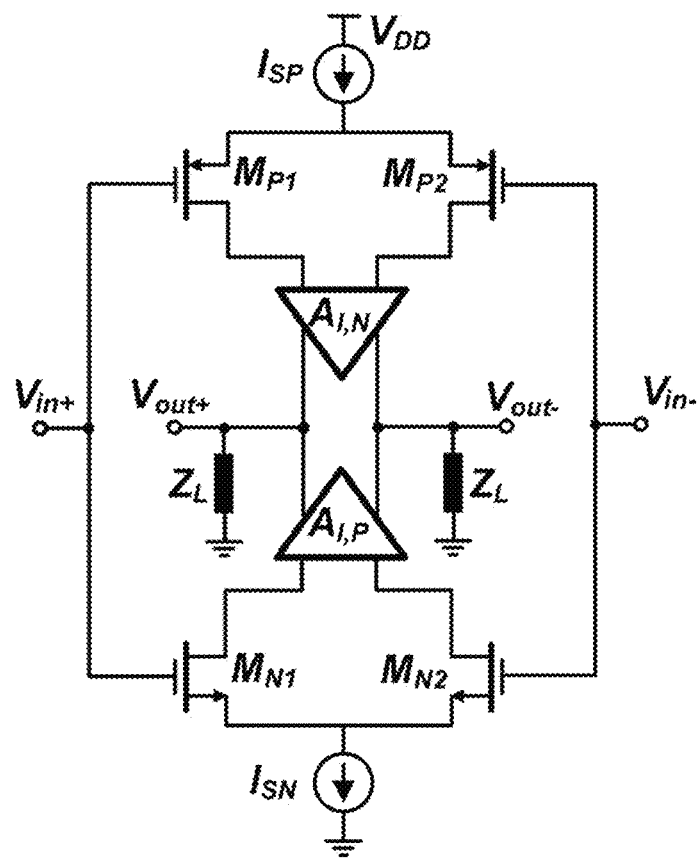
FIG. 4 shows the complementary input structure of the operational transconductance amplifier ("OTA") used in Amplifier I.
Figure 5A:
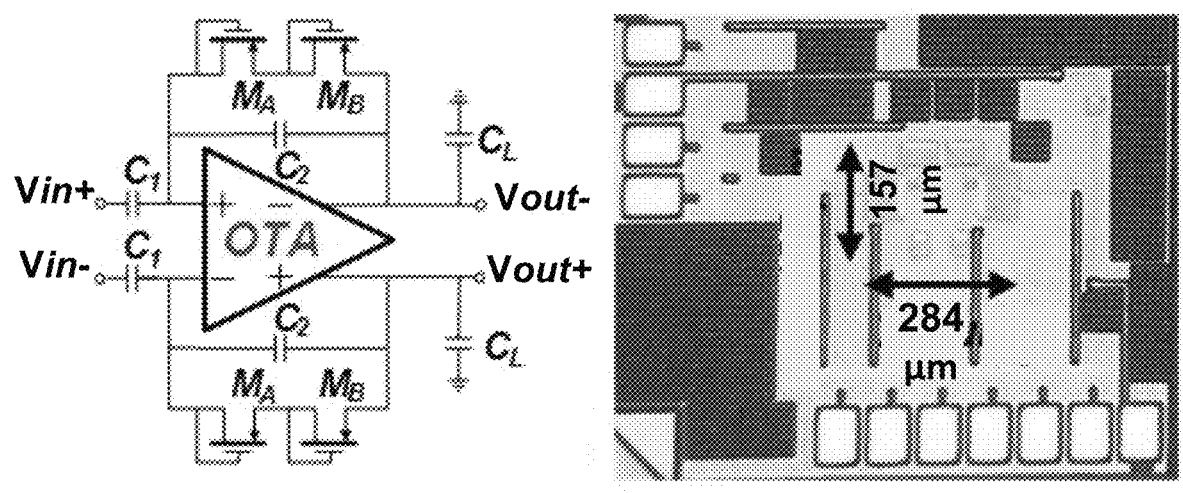
FIG. 5A shows a configuration of Amplifier I comprising a closed-loop amplifier with capacitive feedback and its die micrograph.
Figure 5B:
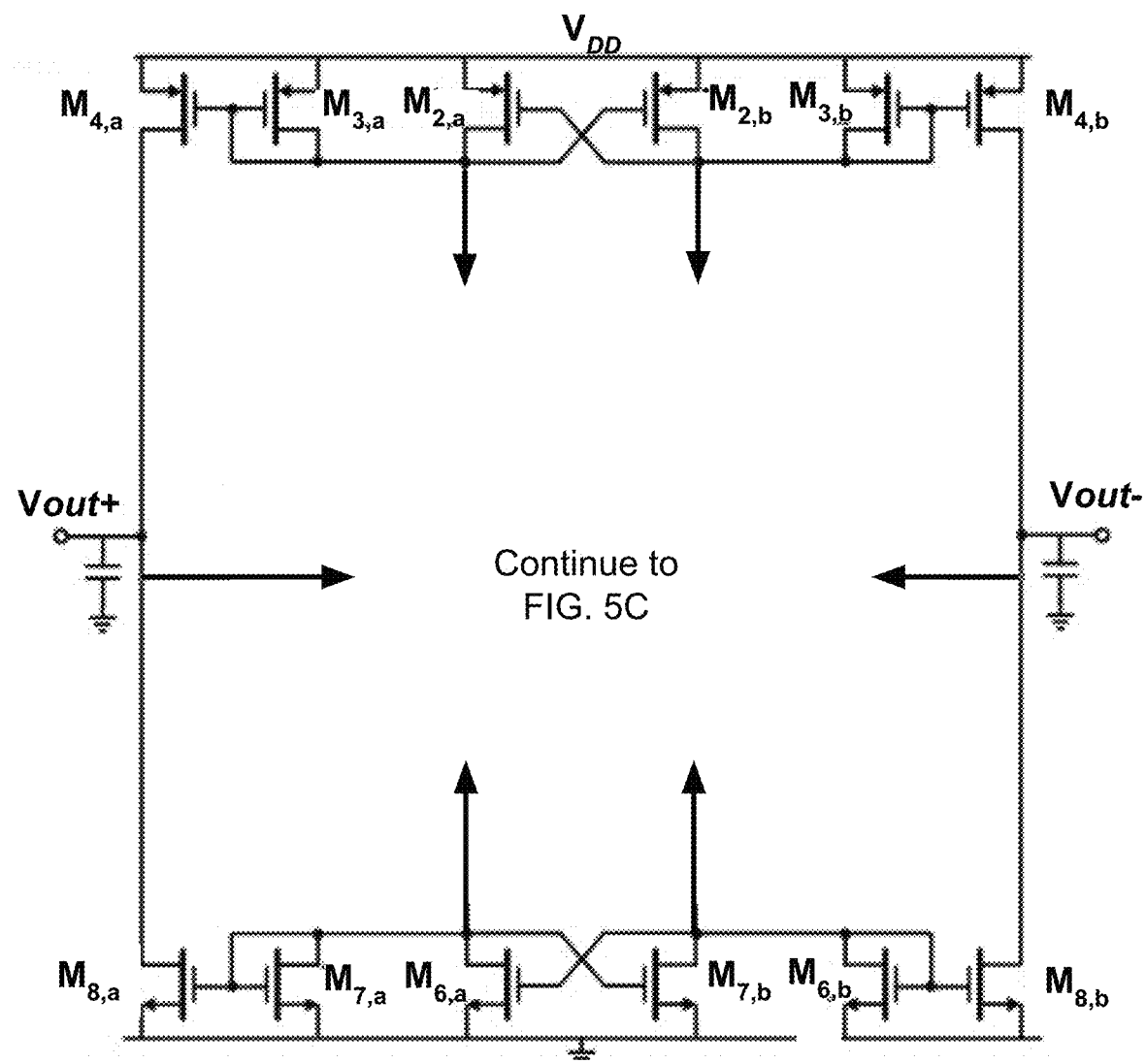
FIGS. 5B-5C shows a schematic of the complementary NMOS-PMOS OTA.
Figure 5C:
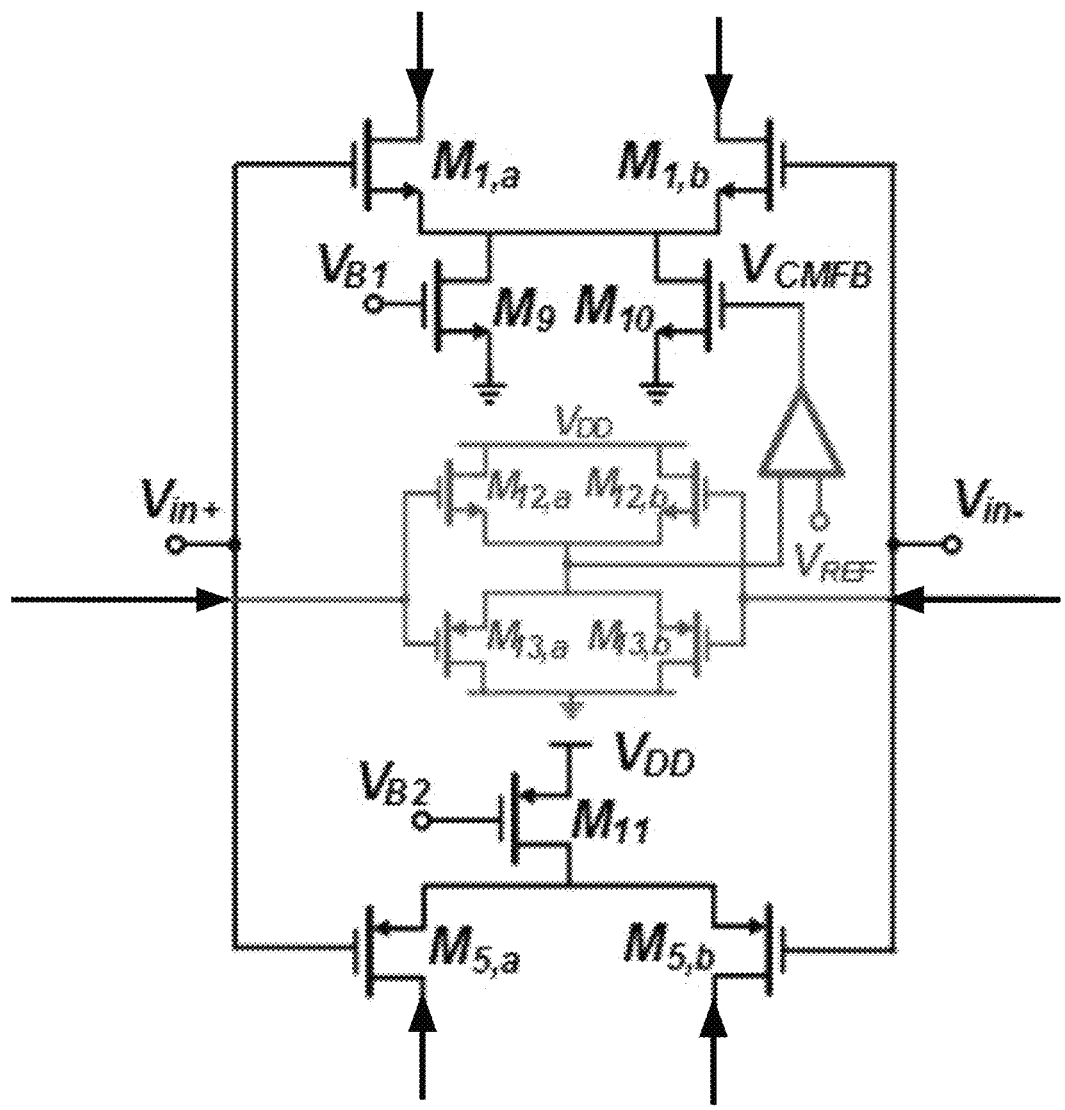
Figure 6:
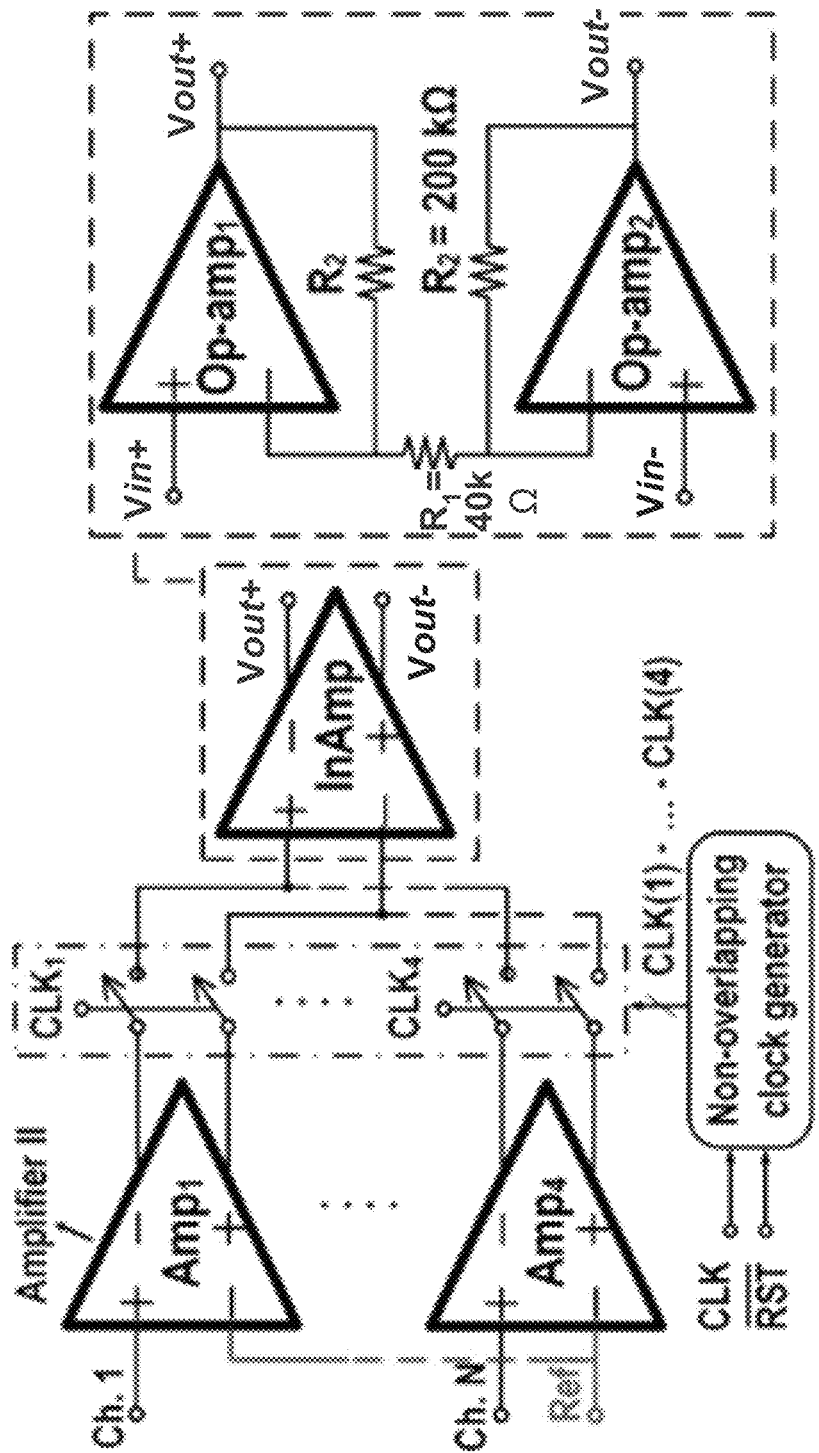
FIG. 6 shows the overall topology of the BSA II including four Amplifier II circuits and one instrumentation amplifier ("InAmp").

BSA I incorporates 64 units of Amplifier I circuits and a serializer, as shown in FIG. 2B, FIG. 4 shows the general block diagram of the OTA, used in the Amplifier I, composed of complementary NMOS-PMOS input stages. Intuitively, the signal is amplified by the transconductance gain of the input transistor pairs and subsequently applied to the current gain stage in each of the top and bottom branches ($A_{I,N}$ and $A_{I,P}$). Upon flowing through the load impedance $Z_L$, the summing current will generate the output voltage, FIG. 5A shows the top-level topology of Amplifier I employing an OTA with an RC feedback network. The AC-coupled input provides DC rejection between the recording electrodes and the OTA input, thus providing a layer of electrical safety and isolation between the patient's brain and the amplifier. FIGS. 5B-5C depict the transistor-level schematic of the OTA utilized in Amplifier I, including common-mode feedback ("CMFB") circuitry (center, in gray). The OTA device sizes and aspect-ratios together with operating points of the individual devices are presented in Table I. NMOS and PMOS transistors' body connections were tied to the ground and supply rails, respectively. The minimum headroom for a single transistor biased in the WI region is ~4$U_T$ (where $U_T \approx 26$ mV at room temperature). As a result, the OTA was biased at 0.4 V supply to mitigate large process variations resulting from the WI operation, while achieving low power and low noise. The first stage employed a complementary NMOS-PMOS differential configuration with a complementary active load comprising parallel combination of diode-connected transistors and a cross-coupled pair. Cross-coupled pair and diode-connected transistors were identically sized as shown in Table I, thereby having the same transconductance. The effective output resistance of the input stage is thus increased from $r_{o3}/(1+g_{m3}r_{o3})\|r_{o1}$ (in the absence of cross-coupled pair load) to $r_{o1}\|r_{o2}\|r_{o3}$, where $r_{o1}$, $r_{o2}$, and $r_{o3}$ are the drain resistances of $M_1$, $M_2$, and $M_3$, respectively. The active-load devices were sized in a way that no instability or latch-up would happen due to the process variation. The size of output transistors $M_4$ and $M_8$ were chosen to exhibit a large drain resistance and a low current consumption at the output stage.

The capacitance ratio $C_1/C_2$ ($C_1$=20 pF and $C_2$=200 fF) defines the closed-loop gain with high accuracy as long as the open-loop gain is sufficiently high. The high output impedance of the OTA imposes a high impedance load for the feedback and next stage circuits. Pseudo-resistors realized by transistors $M_A$ and $M_B$ provide large equivalent resistance R (of few GΩ) to self-bias the input stage of the OTA without consuming any additional power for closing the loop, and set the lower 3-dB cut-off frequency ($f_L$ = $(2\pi RC_2)^{-1}$). Compared to pseudo-resistors used in previous work, this implementation provides a wider linear range of operation. Assuming all transistors are identically matched (to simplify the analysis), the IR Noise power spectral density ("PSD") of the open-loop OTA $\overline{V_{in,OTA}}^2$, is calculated to be:

$$\overline{V_{in,OTA}^2}(f) = \quad (1)$$

$$\frac{4kT\gamma}{g_{m1}}\left(1 + \frac{2g_{m2}}{g_{m1}}\right) + \frac{K_{p,1/f}}{C_{ox}(WL)_1} \times \frac{1}{f}\left[1 + 2\frac{K_{n,1/f}}{K_{p,1/f}}\frac{(WL)_1}{(WL)_2}\left(\frac{g_{m2}}{g_{m1}}\right)^2\right]$$

Here, k is the Boltzmann constant, $\gamma$, $K_{p,1/f}$ and $K_{n,1/f}$ are technology-dependent parameters, f is frequency, $C_{ox}$ is the gate oxide capacitor, and T is the temperature, $\gamma$, the excess thermal noise factor, is slightly lower in the WI region than in the strong inversion ("SI") region. Note that the complementary structure used in this OTA doubles the overall $G_m$. Flicker noise and mismatch effects are slightly attenuated by large input transistors and symmetrical circuit layouts. In addition, dynamic compensation techniques such as chopper stabilization and auto-zeroing are commonly used to reduce the effect of an amplifier offset and flicker noise. However, these techniques require switches with low on-resistance to accommodate highly linear operation for auto-zeroing techniques and low residual input-referred offset voltages for chopping techniques. Thus, a high-swing, on-chip clock needs to be generated at the expense of high power consumption. Therefore, these compensation techniques have not been used in the current design. The IR Noise of Amplifier I in FIG. 5A, $B_{in,tot}^2$, is calculated to be:

$$\overline{V_{in,tot}^2}(f) = (4kTR + \overline{V_{in,OTA}^2}(f))\left(\frac{f_L}{G_C f}\right)^2 + \overline{V_{in,OTA}^2}(f)\left(\frac{C_1 + C_2 + C_{in}}{C_1}\right)^2 \quad (2)$$

Here, G is the midband closed)-loop gain defined by $C_1/C_2$ and $C_{in}$ is the equivalent input capacitance seen from the input of the OTA.

Sizing of the input transistors is critical due to existing trade-off between $\overline{V_{in,OTA}^2}$ and $V_{in,tot}^2$. More precisely, large input transistors with low flicker noise will reduce $\overline{V_{in,OTA}^2}$. On the other hand, a larger device size leads to larger input capacitance $C_{in}$, which adversely affects the system sensitivity. Another point to consider is that $C_{in}$ shunts the gate of the input transistor to ground, causing a capacitive voltage division between $C_1$, $C_2$ and $C_{in}$. This, in turn, lowers the differential loop-gain, thereby preventing the closed-loop gain from being accurately defined. Moreover, as $f_L$ decreases, the thermal noise contribution of the pseudo-resistors to $V_{in,tot}^2$ is reduced, while the flicker noise contribution of the OTA to $V_{in,tot}^2$ is increased.

The serializer in FIG. 2B is clocked at 64 kHz and is composed of custom-designed 6-bit synchronous binary counter, a 6-to-64 decoder and 2×84 complementary pass-gate switches for selecting the amplifier channels. A reset signal puts the circuit in an initial state (channel 64) and the clock signal selects the channels sequentially.

BSA II An Array of 4 Amplifier II Circuits, a Serializer, and an Instrumentation Amplifier The existence of two signal paths in the Amplifier I circuit leads to a degradation in CMRR ($\approx$60 dB). To further elaborate, suppose that the only existing mismatch is between each of the input pairs in FIG. (i.e., $\Delta g_{m_N}$ and $\Delta g_{m_P}$). This mismatch directly contributes to the common-mode to differential-mode gain for the Amplifier I circuit, which is derived as follows:

$$A_{cm-dm} \approx \frac{\Delta g_{m_N} \times A_{I_P} Z_{out}}{(g_{m_{N1}} + g_{m_{N2}})Z_{S_N}} + \frac{\Delta g_{m_P} \times A_{I_N} Z_{out}}{(g_{m_{P1}} + g_{m_{P2}})Z_{S_P}} \quad (3)$$

Figure 7A:
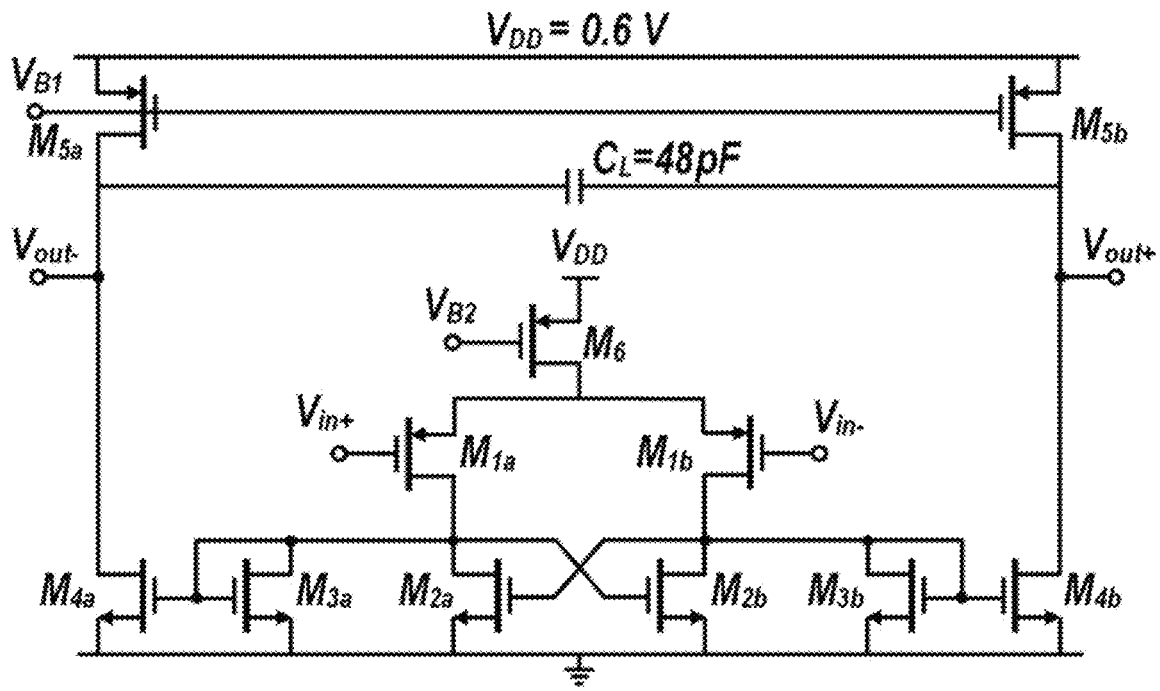
FIG. 7A shows the OTA schematic used in Amplifier H.

Here, $Z_{out}$, $Z_{S_N}$ and $Z_{S_P}$ are output imimpedances of Amplifier I, $I_{S_N}$, and $I_{S_P}$, respectively. It is inferred from (3) that the CMRR of Amplifier I can statistically be degraded by a factor of 2 compared to an amplifier with a single path from the input to the output. A high CMRR is important in brain signal amplifiers due to the presence of a strong 60 Hz power-line noise in the amplification band. If not eliminated, major degradation in the output signal-to-noise ratio ("SNR") will be seen. To further improve this feature, FIG. 6 introduces the block diagram of BSA II, which is composed of an array of 4 Amplifier II circuits, a serializer, and an instrumentation amplifier ("InAmp"). Similar to Amplifier I, Amplifier II is realized as a fully differential RC feedback circuit incorporating 200 fF feedback and 18 pF input AC-coupled capacitors. The matching accuracy of the feedback capacitor limits the achievable CMRR. For instance, it is readily shown that for a closed-loop gain of 100 and 10% mismatch of the feedback capacitor, CMRR is lower than 60 dB. The open-loop OTA within Amplifier II employs PMOS input differential-pair with NMOS cross-coupled active loads, as shown in FIG. 7A. Having one signal path from the input to the output relaxes the mismatch considerations present in the complementary signal paths used in the first design. The IR Noise of the open-loop OTA is calculated to be:

$$\overline{V_{in,OTA}^2}(f) = \quad (4)$$

$$\frac{8kT\gamma}{g_{m1}}\left(1 + \frac{2g_{m2}}{g_{m1}}\right) + \frac{2K_{p,1/f}}{C_{ox}(WL)_1} \times \frac{1}{f}\left[1 + 2\frac{K_{n,1/f}}{K_{p,1/f}}\frac{(WL)_1}{(WL)_2}\left(\frac{g_{m2}}{g_{m1}}\right)^2\right]$$

Assuming a single-pole frequency response, it is readily proven that the noise efficiency factor ("NEF") reaches a lower-limit of $2(n\gamma)^{1/2}$ (where n denotes the subthreshold slope factor) for both OTAs used in Amplifiers I and II if no dynamic compensation techniques are employed. The use of the same closed-loop architecture as in Amplifier I indicates that the IR Noise of Amplifier II is also expressed by (2). The InAmp, after the serializer, provides further amplification and buffering to the output. It is commonly known that isolated resistive feedback circuitry ($R_1$ and $R_2$) provides flexibility in the design of an InAmp (and its constituent, open-loop op-amps) with no concern of loading on preceding circuits. In addition, any variation in $R_1$ is widely known to only contribute to the differential gain variation and will not increase the common-mode to differential-mode gain ($A_{cm-dm}$). Therefore, the CMRR is not degraded. As for the contribution of the mismatch between the $R_2$ resistors ($R_{2\Delta}=R_2+\Delta R$) on CMRR, the InAmp's $A_{cm-dm}$ induced by this mismatch is derived from:

$$A_{cm-dm} = \frac{E_{CM} - 1}{1 + \frac{R_{2\Delta}}{R_1 A_{dm2}} - \frac{R_{2\Delta}}{A_{dm1} R_1} E_{CM} + \frac{1}{A_{dm2}}} \quad (5)$$

where, $$E_{CM} = \frac{1 + \frac{1}{A_{dm2}}\left(1 + \frac{R_2 + R_{2\Delta}}{R_1}\right)}{1 + \frac{1}{A_{dm1}}\left(1 + \frac{R_2 + R_{2\Delta}}{R_1}\right)} \quad (6)$$

In deriving (5), the open-loop gains of the op-amps, Adm1 and $A_{dm2}$, are assumed to be finite, while each op-amp exhibits negligible differential to common-mode gain. The common-mode gain $A_{cm}$ of the InAmp is almost unity. If followed by a high-CMRR amplification stage, the contribution of $A_{cm}$ on CMRR will be negligible. On the other hand, to reduce the impact of $A_{cm-dm}$ on CMRR, the op-amps need to exhibit large open-loop gain. Large open-loop gain significantly reduces the contribution of the $R_2$ mismatch on the CMRR. Ideally, if the op-amps are perfectly matched ($A_{dm1}=A_{dm2}$), $A_{cm\text{-}dm}$ would become zero regardless of the $\Delta R$ value.

The Amplifier II circuit and the InAmp are DC-coupled, eliminating the need for large coupling capacitors. For a 39-dB gain of the OTA, the expected differential input amplitude of the InAmp is less than 9 mV, which falls within the input common-mode range of the InAmp (0 to $V_{DD}-2V_{DS,sat}$ where $V_{DS,sat}$ is the drain-source saturation voltage).

Figure 7B:
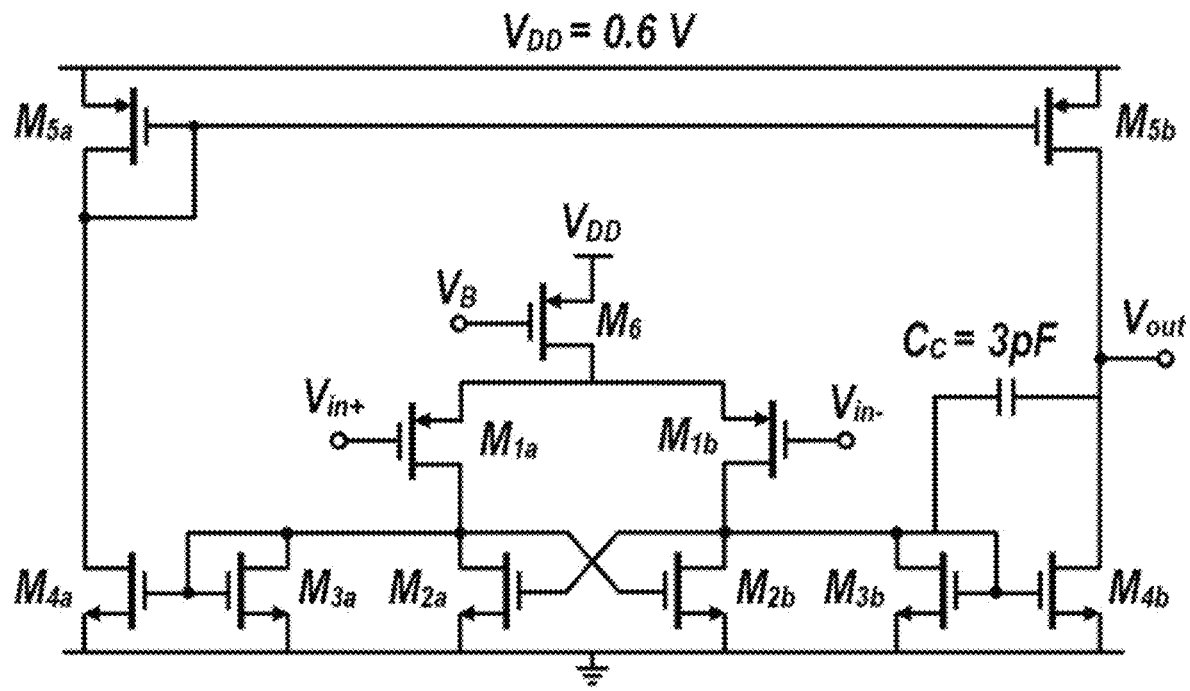
FIG. 7B shows the op-amp schematic used in InAmp.

FIGS. 7A and 7B show the transistor-level schematics of the OTA used in Amplifier II and the op-amp used in InAmp, respectively. Both amplifiers use similar topology while the devices are sized according to the performance specs needed from each circuit, namely, low noise and high transconductance for the OTA (high driving power and high voltage gain for the op-amp). Tables II and III show device sizes and operating points for the OTA and the op-amp, respectively. All transistors were biased in the WI region to maximize power efficiency. To achieve a maximum ECoG bandwidth of 200 Hz in the OTA and avoid out-of-band noise accumulation, a large 48 pF capacitor $C_L$ was placed differentially at the output. The input transistors operate in the deep WI region to maximize their $g_m/I_D$ ratio to reduce the IR Noise contributions of active-load devices ($M_{2a}$-$M_b$ and $M_{3a}$-$M_{3b}$). PMOS transistors were used in the input differential pair to have a lower flicker noise. Furthermore, the use of a PMOS input pair for the op-amp makes common-mode levels of the OTA output and the op-amp input compatible, thereby making it possible to DC-couple the two. DC-coupling eliminates the need for large decoupling capacitors as well as biasing circuitry of the op-amp inputs. The OTA bandwidth and stability are determined by its output stage where the dominant pole is located. On the other hand, the op-amp's dominant pole is located at the output node of its first stage, as its output stage should provide high current drive capability. The op-amp is thus Miller-compensated and its bandwidth is chosen to be ≈800 Hz in order to accommodate 4 recording channels.

Figure 8:
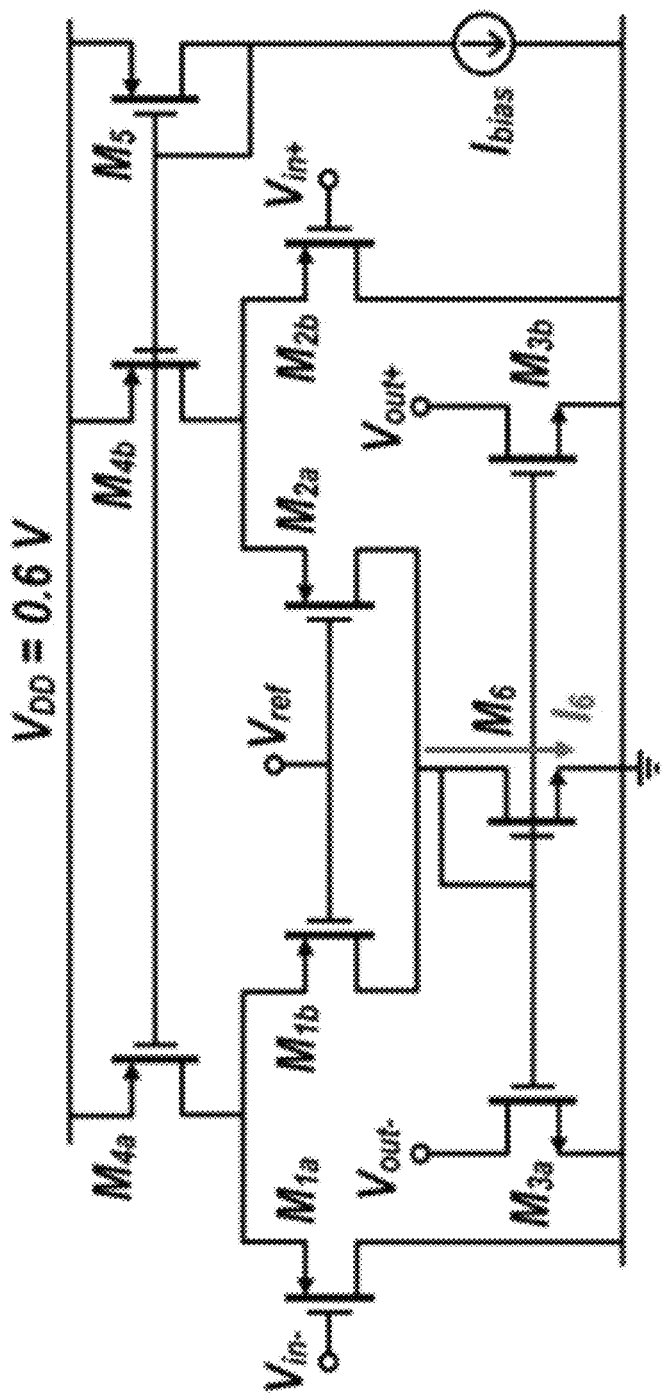
FIG. 8 shows the common-mode feedback ("CMFB") circuit used in Amplifier H.

FIG. 8 shows the proposed CMFB circuit to set the output common-mode voltage of the OTA. The drain currents of transistors $M_{4a}$ and $M_{4b}$ are steered to ground or to transistor $M_6$, depending on common-mode level of $V_{in}$. $M_{3a}$ and $M_{3b}$ mirror $M_6$, sinking current from the OTA's output stage, thereby adjusting the OTA common-mode level. Note that the input and the output of the CMFB are physically connected together. The CMFB output currents are expressed as:

$$A_{cm\text{-}dm} = \frac{E_{CM} - 1}{1 + \frac{R_{2\Delta}}{R_1 A_{dm2}} - \frac{R_{2\Delta}}{A_{dm1} R_1} E_{CM} + \frac{1}{A_{dm2}}} \quad (7)$$

Here, $g_{m1,2}$ denotes the transconductance of $M_{1a}$-$M_{1b}$ and $M_{2a}$-$M_{2b}$, $W_3$ is the channel width of $M_{3a}$ $M_{3b}$, and $W_6$ is the width of $M_6$. Input transistors ($M_{1a}$-$M_{1b}$ and $M_{2a}$-$M_{2b}$) should remain in the saturation region for proper operation of the CMFB.

Having a swing of a few millivolts at the OTA's output ensures that no transistor leaves saturation. Transistors $M_{3a}$ and $M_{3b}$ were designed to have a long channel length, with negligible loading effect on the OTA. Their parasitic capacitances were absorbed in the OTA's load capacitor. The simulation of the CMFB showed a current consumption of 24 nA and a common-mode phase margin of at least 35°.

Figure 9:
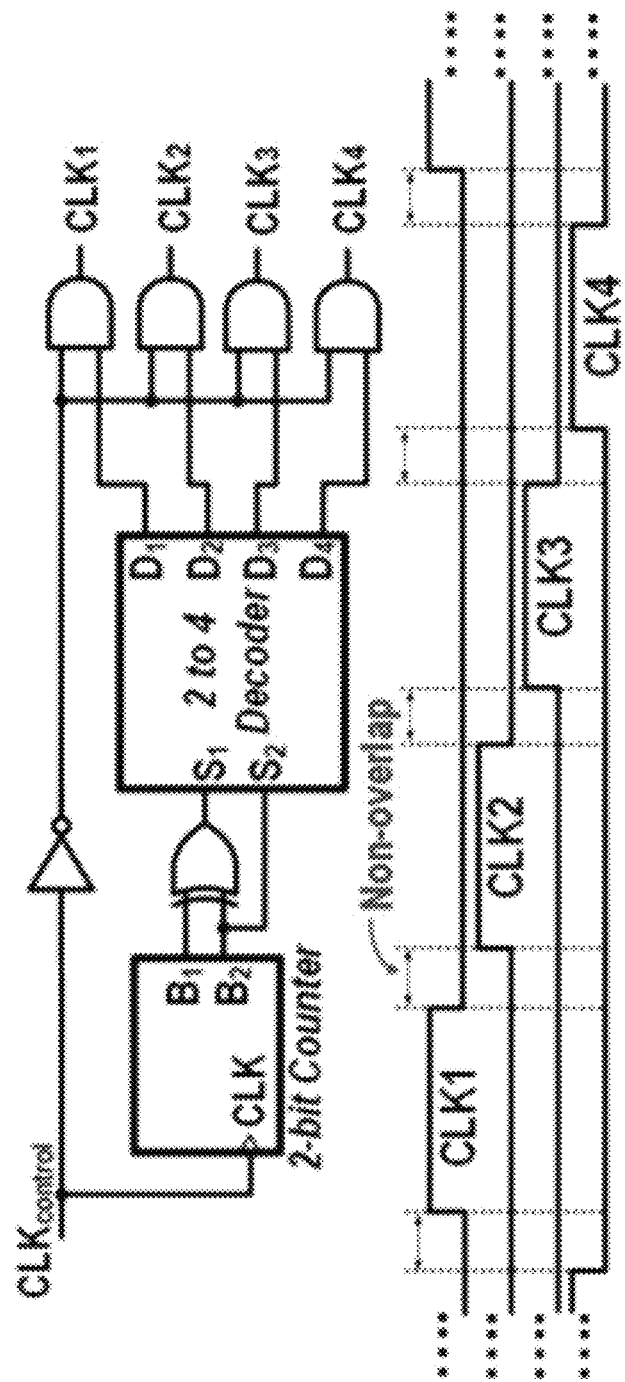
FIG. 9 shows non-overlapping clock signals applied to the serializer switches.

The circuitry for the serializer logic used in BSA II is presented in FIG. 9. This logic contrives i) non-overlapping clock signals for time-multiplexing, and ii) a gray-coding scheme for a 2-bit binary counter to eliminate race conditions. The serializer clock, signal's duty-cycle produces temporal spacing between clocks applied to the serializer switches (FIG. 9). A Gray-code converter is used to convert binary code to Gray code such that the counter exhibits no race condition, which could otherwise result in sparks in the 2-to-4 decoder of FIG. 9. A T-network switch was used for channel selection in this serializer to provide large input-output isolation and minimize the effects of charge-injection and clock-feedthrough.

Measurements

A. Electrical Measurements

Figure 12A:
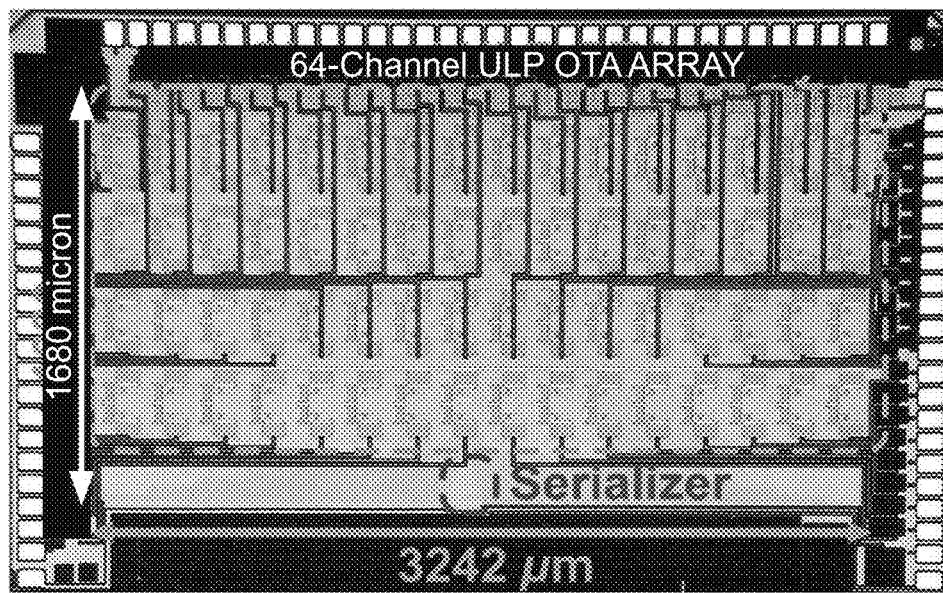
FIG. 12A shows a die microphotograph of the BSA I with 64-channel amplifier array and serializer.
Figure 12B:
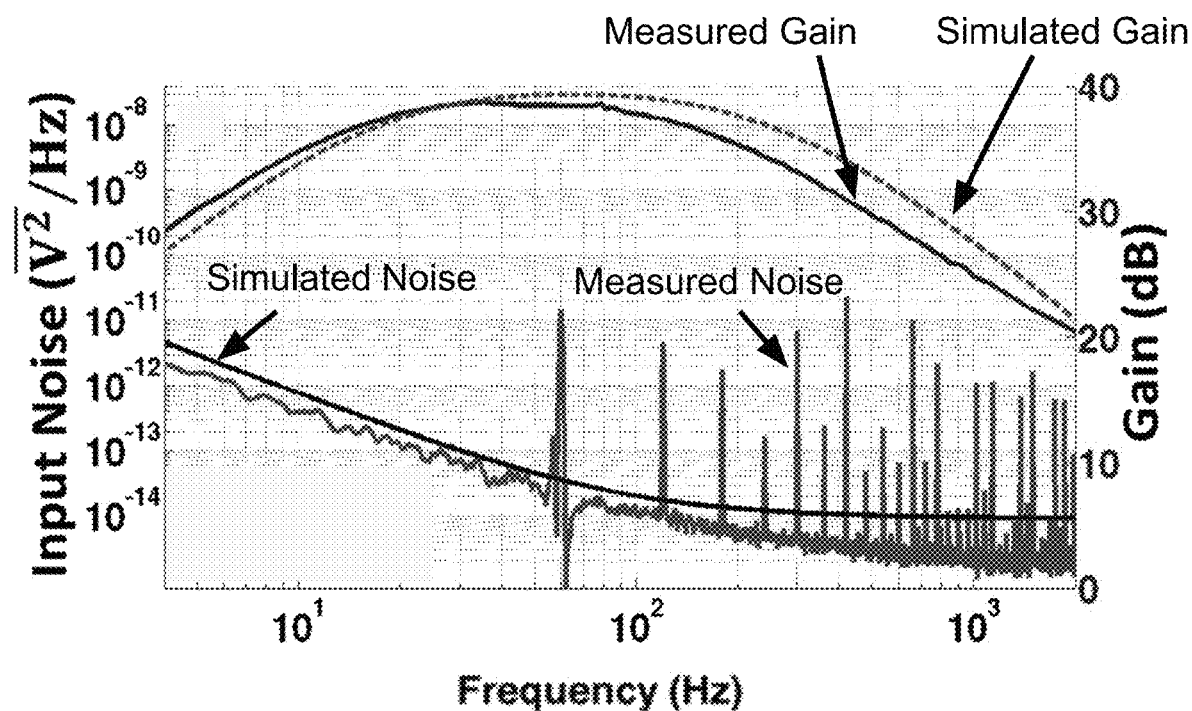
FIG. 12B shows measured and simulated Amplifier I gain and noise responses. Note that the sharp peaks were due to 60 Hz harmonics on the unshielded cables.
Figure 13A:
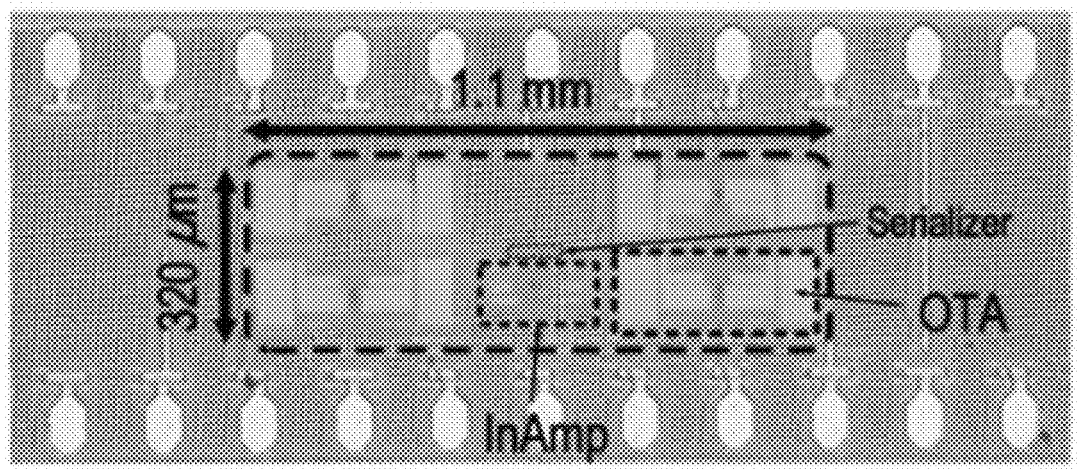
FIG. 13A shows the die microphotograph of the BSA II with 4-channel amplifier array and serializer.
Figure 13B:
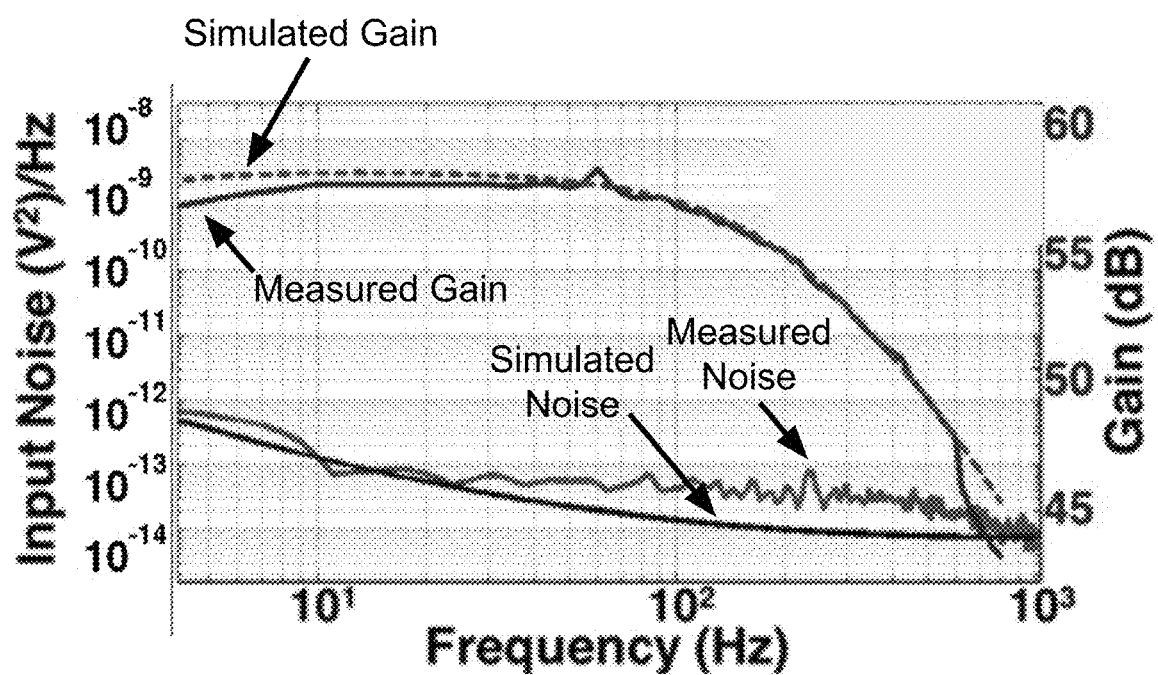
FIG. 13B shows measured and simulated gain and noise responses for a single channel of BSA II.

Amplifiers I and II were fabricated in 130 nm and 180 nm CMOS processes, occupying 0.044 mm²/0.052 mm² die areas, and consuming 0.216 µQ/0.69 µW from 0.4V/0.6V externally provided supply voltages, respectively. FIGS. 12A and 13A show die microphotographs of BSA I and BSA II front-end circuits. The first chip (BSA I) occupies 5.45 mm², and the second chip (BSA II) occupies 0.352 mm² excluding pad rings). The pad ring incorporates a 2 kV HBM ESD protection circuitry with negligible leakage current. The BSA I prototype uses an off-chip buffer to drive a commercial signal acquisition unit (MP150 with 12-bit ADC, Biopac Systems Inc. Goleta, Calif.). The overall amplification gain for the BSA I and BSA II AFEs were measured using an Agilent 33250A waveform generator and SMA attenuators, each providing 39/58 dB voltage gain and an IR Noise of ~2.19/2.3 $\mu V_{RMS}$ across 12-190 Hz/2-175 Hz of operation bandwidth, respectively (FIGS. 12B and 13B). Without an explicit calibration scheme, the lower-cutoff frequency is not well controlled across process corners. In this work, the frequency was chosen to be smaller than the 8-Hz corner frequency of α-band, with negligible effects on noise performance. Simulations show that this lower-cutoff frequency varies from 2 to 10 Hz across process corners.

The 60 Hz interference and its harmonic were removed from the noise plot and calculations in FIG. Linearity and noise measurements were done using Agilent E4448a spectrum analyzer. A low noise off-the-shelf instrumentation amplifier (AD620) was used to boost the noise level and drive the spectrum analyzer. The calculated dynamic range of the Amplifier I at 37 Hz, for ~1% Total Harmonic Distortion ("THD") was 58 dB. The Amplifier II harmonics for 0.2 mV input voltage at 47 Hz (which is 2 times higher than the expected neural signal amplitude) was lower than the measured noise floor, indicating linear operation. For 150 MVpp signal at 60 Hz, Amplifier I/II exhibited a CMRR greater than 60 dB/74 dB and a PSRR greater than 58 dB/70 dB, respectively. Table IV provides the performance summary of the designed amplifiers and a comparison with relevant art from academia and industry.

B. Human Neurological Measurements

This study was approved by the Institutional Review Boards of the University of California, Irvine and the Rancho Los Amigos National Rehabilitation Center, and is considered of non-significant risk. Three human subjects provided informed consent to participate. The chip was powered by a current-limited (2 mA) supply source. The hospital instruments were disconnected to avoid creation of any unwanted electrical loops. The AC-coupled connection between the electrodes and the amplifiers provided DC isolation.

Figure 14:
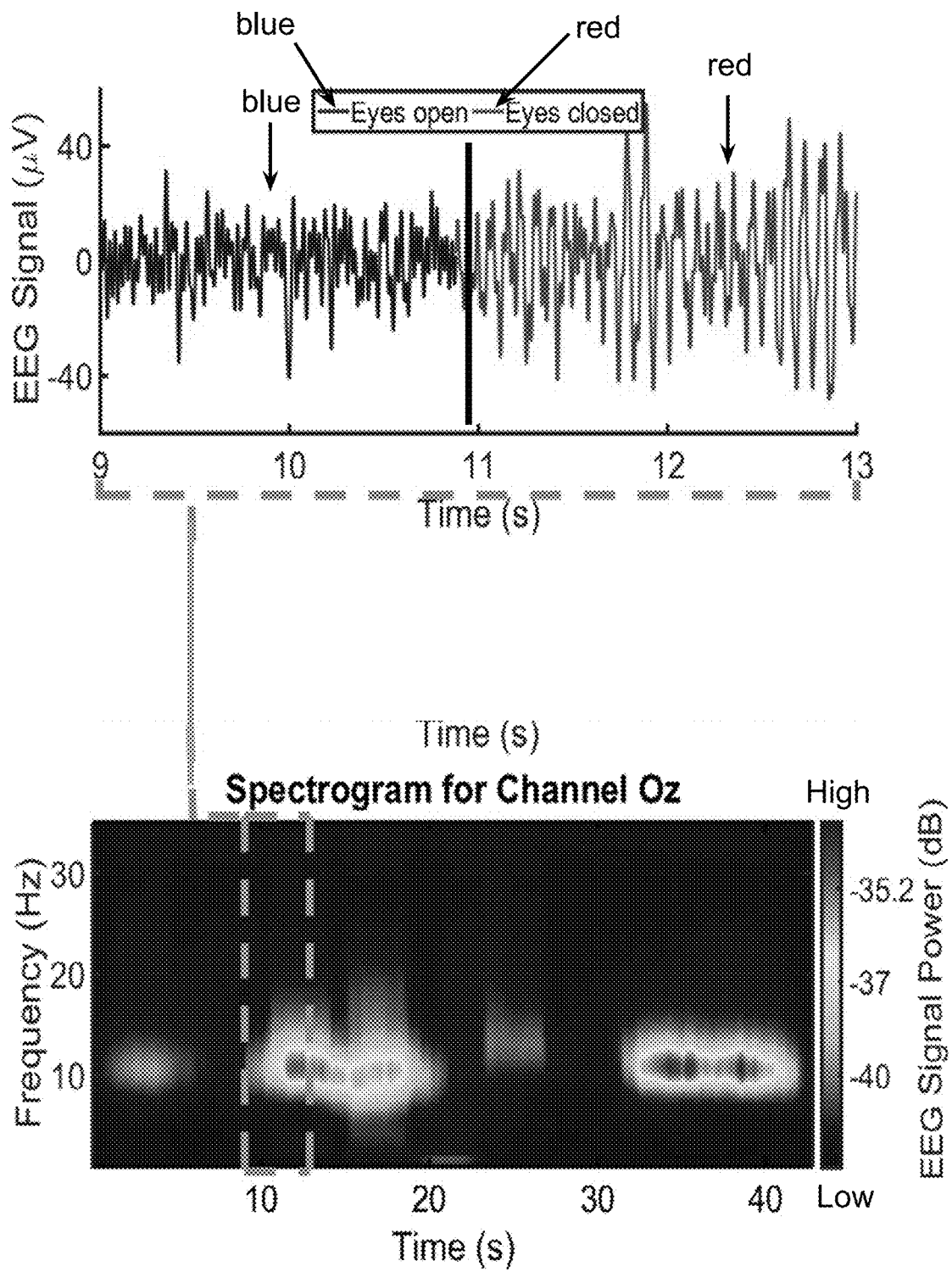
FIG. 14 shows the Amplifier I EEG time series (top) and spectrogram (bottom) from channel Oz with 10 dB increase in the posterior dominant alpha rhythm (8-12 Hz) amplitude when the subject closed his eyes. The subject closed his eyes at 10 and 32 seconds and opened again at 20 and 42 seconds.
Figure 15A:
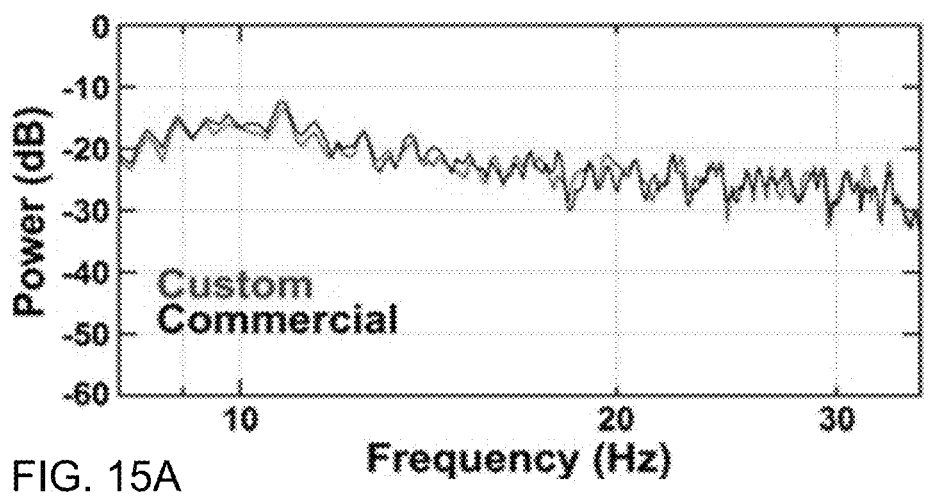
FIG. 15A shows the power spectrum density ('PSD") of the BSA II and commercial bioamplifier from 30 seconds of EEG data.
Figure 15B:
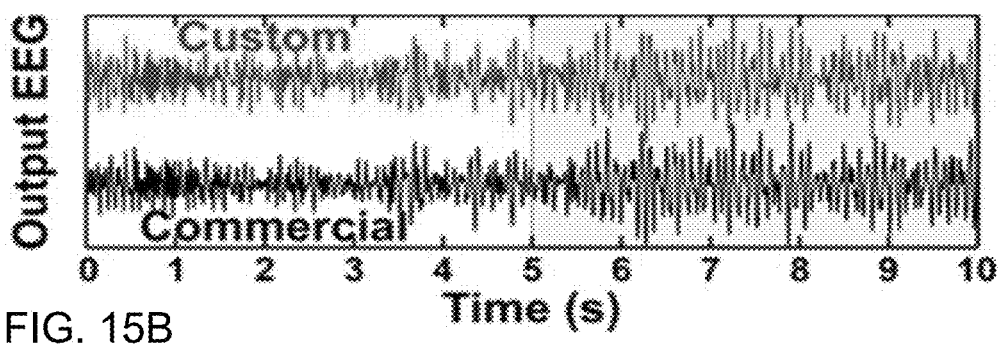
FIG. 15B shows EEG $\alpha/\beta$-band (8-35 Hz) time-series data from channel Oz (referenced to AFz) using the BSA II and commercial bioamplifiers when the subject was instructed to alternate between eyes-open (white background) and eyes-closed (gray background).

1) EEC: For two healthy subjects (males, 26 and 27 years old), the impedances of electrodes AFz, Cz, Pz, and Oz in the 10/10 EEG system were reduced to <3 kΩ using conductive gel. Measurements were performed on one of the subjects using Amplifier I, as follows. EEG signal from Cz, Pz, and Oz (all referenced to AFz) were recorded at 2353.2 Hz per channel using a data acquisition system (Biopac MP150). This sampling rate corresponds to a sampling period of ~100 microseconds per channel. The subject was provided verbal cues to alternate between eye opening/closing every 10 seconds. As a representative example, FIG. 14 shows prominent changes (~10 dB) in the power of the occipital posterior dominant α rhythm at channel Oz in both the time series and the time-frequency spectrogram during this task. The subject closed his eyes at 10 and 32 s and opened again at 20 and 42 seconds. This is consistent with classic neurophysiological findings.

Figure 16:
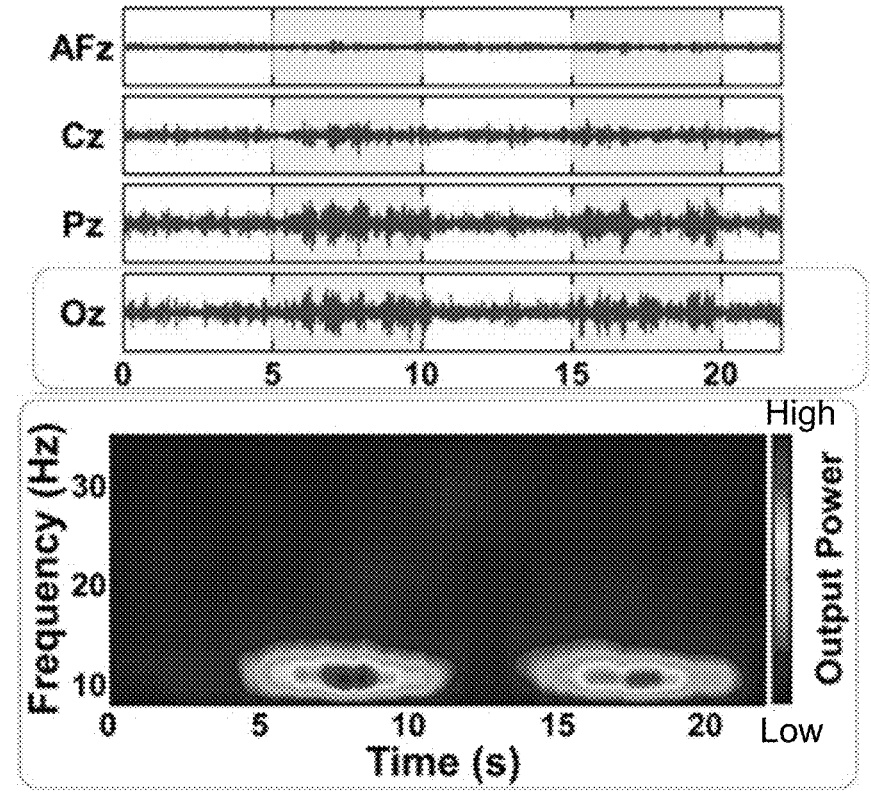
FIG. 16 shows the BSA II EEG $\alpha/\beta$-band (8-35 Hz) time-series data (top) and spectrogram (bottom) from channel AFz, Cz, Pz, and Oz (all referenced to AFz) as the subject was instructed to alternate between eyes-open (white background) and eyes-closed (gray background).

Measurements were performed on the second subject using Amplifier II, as follows. EEG signals from the Oz channel (referenced to AFz) was split to Amplifier II as well as to a commercial bioamplifier (Biopic EEG100C) and sampled at 50 kHz. The output from both systems was down sampled to 2 kHz and filtered into the 8-35 Hz frequencies in software (see FIGS. 15A-15B). The two signals exhibited a Pearson correlation coefficient of 0.89, and their envelope powers exhibited a correlation of 0.93. In addition, multiplexed EEG signals were multiplexed from electrodes AFz, Pz, and Oz (all referenced to AFz) using Amplifier II. The results after de-multiplexing in software are shown in FIG. 16. As physiologically expected, electrodes Oz and Pz exhibit larger amplitudes of the occipital posterior dominant α rhythm during the eyes-closed state.

Figures 17, 18A:
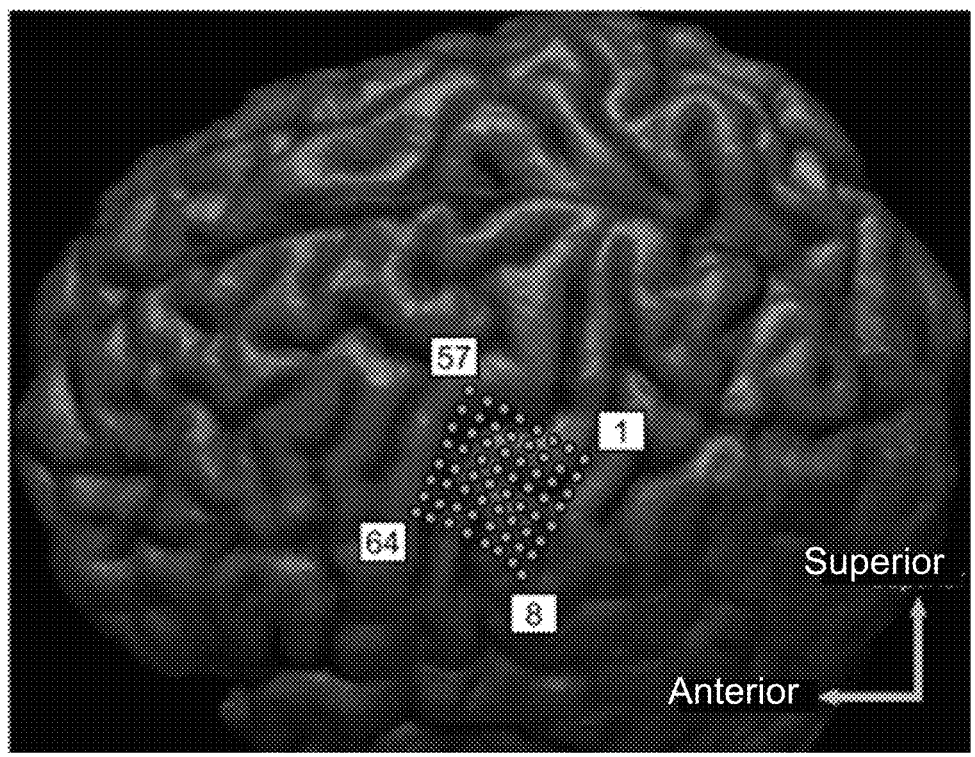
FIG. 17 shows Table III: Op-Amp Device Sizes and Operating Points.
FIG. 18A shows an MRI of the patient with implanted ECoG grid over the left motor cortex, where electrodes 28 and 24 were used as the reference and around, respectively.
Figure 18B:
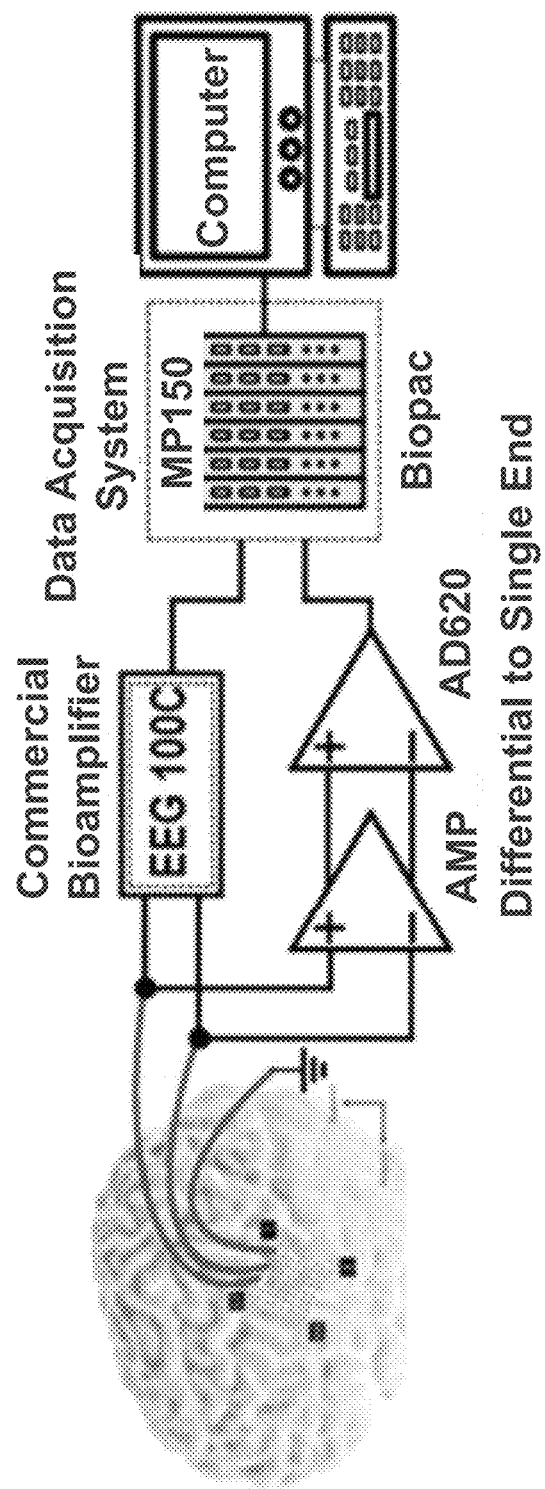
FIG. 18B shows an In vivo ECoG measurement setup.

2) ECoG: One subject (43-year-old male) undergoing ECoG implantation for epilepsy surgery evaluation participated in the study. This subject had an 8×8 grid (Ad-Tech, Racine, Wis.) of 2 mm-diameter electrodes (4-mm center-center spacing) implanted over the primary motor cortex. FIG. 18A shows the locations of the implanted electrodes (derived by co-registering a CT scan and MRI of the head). The subject completed his epilepsy monitoring procedure and was awaiting ECoG grid removal the next day. Hence, the hospital EEG system was disconnected at the time of measurement. ECoG signals were simultaneously routed to Amplifier II and to a commercial EEG100C bioamplifier using unshielded cables as shown in FIG. 18B. A negligible loading effect and source impedance mismatch from EEG100C (2 MΩ input impedance) on Amplifier II was expected due to a relatively small impedance of the electrodes (<1 kΩ). ECoG electrodes' impedance is reported to be stable over time, eliminating the need for a constant monitoring of its value. The output from both amplifiers was recorded at 25 kHz by the MP150 system for 30 seconds. Note that the subject was asleep during this time and did not participate in any associated behavioral task for further verification of the amplifier array.

The resulting signals were then down sampled to 2 kHz in software for further processing. The correlation coefficient between the signals from BSA II and the EEG100C was 0.99 from 8-35 Hz (covering the α and β bands), 0.94 from 35-70 Hz (low-γ band), and 0.72 from 70-120 Hz (high-v band). Moreover, the correlation between each system's envelope power in α/β, low-γ, and high-γ bands, were 0.99, 0.99, and 0.89 respectively. This slight decrement in the high-γ band correlation between the bioamplifiers was expected since the signal power decreases with frequency and approaches the Amplifier II noise floor. A software notch filter was applied on the signal from 57 to 63 Hz before calculating the correlations. A representative PSD of the recorded signals across the α, β, and γ bands (8-120 Hz) and a 10-second output time-series of the BSA II and its commercial counterpart are shown in FIG. 19, demonstrating qualitative similarities between the two. The peaks at 60 Hz for custom and commercial PSDs were caused by the limited CMRR of the signal chain, as well as the coupled power line interference to the unshielded interface between the analog output and the external ADC.

Summary of the System Architecture

Two brain signal acquisition front-ends designed in the region are described herein. Fabricated in 130 nm and 180 nm CMOS 608 processes, each amplifier within each array consumes 0.216/0.69 µW, respectively (not including buffer and InAmp). Measured IR Noise across the bandwidth was 2.19/2.3 $\mu V_{RMS}$ corresponding to NEF of 4.65/7.22 and PEF of 11.7/31.3. An objective comparison of human in vivo EEG and ECoG measurements acquired by the present system and a commercial bioamplifier demonstrated that the BSA I and BSA II were able to record these neural signals reliably. This suggests that the circuit architecture presented in this work can serve as the basis for a highly miniaturized and ultra-low power brain signal acquisition unit. In some embodiments, the front-end can have a low susceptibility to environmental noise by further including, for example, an on-chip analog-to-digital converter. In other embodiments, the front-end may be capable of large interference rejection at low supply voltages in the presence of a sensory feedback stimulation circuitry.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

REFERENCES

[1] Heydari, et al. "A 64-Channel Ultra-Low Power Bioelectric Signal Acquisition System for Brain-Computer Interface." *IEEE Xplore* Biomedical Circuits and Systems Conference (BioCAS), 2015,

[2] J. L. Collinger et al., "High-performance neuroprosthetic control by an individual with tetraplegia," *The Lancet*, vol. 381; no. 9866, pp. 557-564, 2013.

[3] R. Muller, S. Gambini, and J. M. Rabaey, "A 0.013, 5, dc-coupled neural signal acquisition ic with 0.5 v supply," *IEEE J. Solid-State Circuits*, vol. 47, no. 1, pp. 232-243, 2012.

[4] G. Schalk and E. C. Leuthardt, "Brain-computer interfaces using electrocorticographic signals," *IEEE Reviews Biomed. Eng.*, vol. 4, pp. 140-154, 2011.

[5] A. Wang, B. H. Calhoun, and A. P. Chandrakasan, *Sub-threshold design for ultra low-power systems*, Springer, 2006, vol. 95.

[6] M. Daliri and M. Maymandi-Nejad, "Ultra-low voltage common-mode voltage detector circuit," *Electronics Letters*, vol. 44, no. 13, pp. 782-783, 2008.

[7] W. Wattanapanitch, M. Fee, and R. Sarpeshkar, "An energy-efficient micropower neural recording amplifier," *IEEE Trans. Biomed. Circuits Syst.*, vol. 1, no. 2, pp. 136-147, June 2007.

[8] N. Verma, et al., "A micro-power eeg acquisition soc with integrated feature extraction processor for a chronic seizure detection system," *IEEE J. Solid-State Circuits*, vol. 45, no. 4, pp. 804-816, April 2010.

[9] T. Denison et el., "A 2 μw 100 nv/rthz chopper-stabilized instrumentation amplifier for chronic measurement of neural field potentials," *IEEE J. Solid-State Circuits*, vol. 42, no. 12, pp. 2934-2945, 2007.

[10] McCrimmon, et al., "*Electrocorticographic Encoding of Human Gait the Leg Primary Motor Cortex,*" *Cerebral Cortex*, July 2017.

http://www.neuropace.com/the-rns-system/

[11] C. E. King, P. T. Wang, C. M. McCrimmon, C. C. Y. Chou, A. H. Do, and Z. Nenadic, *The feasibility of a brain-computer interface functional electrical stimulation system for the restoration of overground walking after paraplegia, J. NeuroEng. Rehabil.*, vol. 12(80), 2015

[12] A. H. Do, P. T. Wang, C. E. King, S. N. Chun. and Z. Nenadic, *Brain-computer interface controlled robotic gait orthosis, J. NeuroEng. Rehabil.*, vol. 10(111), 2013.

[13] C. E. King, P. T. Wang, L. A. Chui, A. H. Do, and Nenadic, *Operation of a brain-computer interface walking simulator for individuals with spinal cord injury, J. Neuro-Eng. Rehabil.*, vol. 10(77), 2013.

[14] P. T. Wang, C. E. King, L. A. Chui, A. H. Do, and Z. Nenadic, *Self-paced brain-computer interface control of ambulation in a virtual reality environment. J. Neural Eng.*, vol. 9(5), pp. 056016, 2012.

[15] P. T. Wang, E. J. Puttock, C. E. King, A. Schombs, J. J. Lin, M. Sazgar, F. P. K. Hsu, S. J. Shaw, D. E. Millett, C. Y. Liu, L. A. Chuff, A. H. Do, and Z. Nenadic, *State and trajectory decoding of upper extremity movements from electrocorticogram, in Proc. of the 6th Annual international IEEE EMBS Conference on Neural Engineering*, pp. 969-972, 2013.

What is claimed is:

1. A system for direct brain control of a prosthetic, the system comprising:
   a. a neural signal acquisition unit (102), capable of being implanted in the skull of a patient, capable of acquiring a plurality of brain signals and processing them into a data stream, wherein the power of the neural signal acquisition unit (102) is sufficiently low to prevent heating of local tissues, wherein the neural signal acquisition unit (102) comprises an ultra-low power amplifier array and serializer integrated circuit ("IC") (108) capable of low-noise amplification and serialization of the data stream;
   b. a subcutaneous tunneling cable (110), connecting the neural signal acquisition unit (102) and a chest wall unit (101), wherein the subcutaneous tunneling cable (110) comprises one wire for delivering the data stream from the neural signal acquisition unit (102) to the chest wall unit (101);
   c. the chest wall unit (101) incorporating low-power analog-to-digital converter (ADC), digital signal processor (1)SP, low-power wireless transceiver, wireless charging unit, and memory, embedded on a centimeter-scale system and implantable in the body of a patent, capable of multitude of operations including digitization and decoding of serialized neural signals coming from the neural signal acquisition unit (102), receiving the data stream from the signal acquisition unit, processing the data stream into a set of real time commands and transmitting the command to a remote prosthetic; and
   d. a battery (11.1), integrated into the chest wall unit (101), capable of providing power to the chest wall unit (101) and the neural signal acquisition unit (102), wherein the battery (111) is wirelessly rechargeable;
   wherein a total power consumption of the system is less than 30 mW.

2. The system of claim 1 further comprising an amplifier array operatively coupled to the neural signal acquisition unit (102) for amplifying the plurality of brain signals acquired to be delivered to the chest wall unit (101), wherein the amplifier array and neural signal acquisition unit (102) are ultra-low power ("ULP") components.

3. The system of claim 1, wherein the chest wall unit (101) is a low power DSP (105).

4. The system of claim 1, wherein the chest wall unit (101) further comprises a low power analog to digital converter ("ADC") (103), wherein the ABC (103) is operatively connected to the neural signal acquisition unit (102) and the tunneling cable (110), wherein the ADC (103) is configured to digitize the data stream received from the neural signal acquisition unit (102).

5. The system of claim 1, wherein the neural signal acquisition unit (102) communicates with an external computer via the wireless transceiver (109).

6. The system of claim 1, wherein the wireless transceiver is a low-power radio frequency (RF) transceiver (109).

7. A system from direct brain control of a prosthetic, the system comprising:
   a. a neural signal acquisition unit (102), capable of being implanted in the skull of a patient, comprising:
      i. a plurality of electrodes, capable acquiring a plurality of brain signals;
      ii. a serializer integrated circuit, operatively connected to the plurality of electrodes, capable of receiving the plurality of brain signals, converting them into a data stream, and serializing the data stream, wherein the power of the integrated circuit is sufficiently low to prevent heating of local tissues,
   b. a subcutaneous tunneling cable (110), connecting the neural signal acquisition unit (102) and a chest wall unit (101), capable of supplying power from the chest wall unit (101) to the neural signal acquisition unit (102), capable of transmitting the data stream from the neural signal acquisition unit (102) to the chest wall unit (101), wherein the subcutaneous tunneling cable (110) comprises one wire for transmitting the data stream from the signal acquisition unit (102) to the chest wall unit (101);

c. the chest wall unit (101), capable of being implanted in the body of a patient, comprising:
 i. a processor (105);
 ii. a memory module (107) operatively coupled to the processor (105), said memory module (107) storing a set of instructions comprising:
  1. receiving a data stream from the neural signal acquisition unit (108);
  2. processing the data stream to produce a set of real-time commands through a low-power analog-to-digital converter (ADC);
  3. transmitting the real-time commands to the prosthetic via a wireless transceiver (109), wherein the wireless transceiver (109) communicates with a prosthetic;
 iii. the wireless transceiver (109) operatively coupled to the processor (105);
 iv. a battery (111) providing power to the chest wall unit (101) and the neural signal acquisition unit (102), wherein the battery (111) is wirelessly rechargeable; and
 v. the ADC capable of processing the data stream to produce the set of real-time commands;
 wherein a total power consumption of the system is less than 30 mW.

8. A fully-implantable brain-computer interface system for acquiring and analyzing electrocorticogram ("ECoG") signals from a brain of a patient to enable direct brain control of a prosthetic, the system comprising:
a. a bioelectric signal acquisition system (102), referred to herein as a skull unit, configured to be fully implanted into a skull of the patent, wherein the skull unit 102) comprises:
 i. an ECoG grid (104) comprising a plurality of electrodes configured to acquire the ECoG signals;
 ii. an ultra low-power ("LLP") amplifier array (106), operatively coupled to the ECoG grid (104), configured to amplify the ECoG signals acquired; and
 iii. a ULP serializer integrated circuit ("IC") (108) operatively coupled to the ULP amplifier array (106);
b. a chest wall unit (101) configured to be implanted within a chest wall of the patient comprising:
 i. a low-power analog-to-digital converter ("ADC) (103);
 ii. a low-power digital signal processor ("DSP") (105) operatively coupled to the low-power ADC (103) (~25 mW combined);
 iii. a memory module (107) operatively coupled to the low-power DSP (105), said memory module (107) storing a set of instructions for execution by the low-power DSP (105);
 iv. a low-power radio frequency transceiver ("RF TRX") (109) operatively coupled to the low-power DSP (105); and
 v. a battery (111) providing power to the low-power ADC (103), the low-power DSP (105), the memory module (107), and the low-power RF TRX (109), wherein the battery is wirelessly rechargeable; and
c. a subcutaneous tunneling cable (110), operatively coupling the ULP serializer IC (108) of the skull unit (102) to the low-power ADC (103) of the chest wall unit (101);

wherein said tunneling cable (110) also provides power from the battery (111) to the ULP serializer IC (108) and the ULP amplifier array (106), thus making the skull unit (102) a battery-less system, wherein, as the LLP amplifier array (106) and the ULP serializer IC (108) are both ULP components, power consumption by the skull unit (102) is sufficiently low for prevent heating of local tissues, wherein after amplification of the ECoG signals via the LLP amplifier array (106), the amplified ECoG signals are serialized by the ULP serializer IC (108) to produce a serialized data set, which is router to the chest wall unit (101) via the tunneling cable (110), wherein, as the ECoG signals are serialized prior to transmission to the chest wall unit (101), a number of wires comprising the tunneling cable (110) is effectively reduced to at least one, wherein the serialized data set is digitized by the low-power ADC (103) and subsequently transmitted to the low-power DSP (105) for de-serialization and digital re-timing to produce a data set for processing, wherein the data set is processed via the low-power DSP (105) or via an external computer, wherein said processing via the low-power DSP (105) comprises an execution of the set of instructions, resulting in a plurality of real-time commands, said commands are wirelessly transmitted to the prosthetic via the low-power RF TRX (109), wherein the prosthetic executes said commands and performs tasks associated with said commands, wherein the plurality of electrodes are implanted in a subdural space of the brain to allow a plurality of tissue layers to separate the plurality of electrodes from cortical tissue, wherein said subdural implantation effectively prevents scar tissue formation and dissolution of the plurality of electrodes, thus providing ECoG signal stability as compared to an intracortically implanted microelectrode that is subject to scar tissue formation and dissolution of said microelectrode, resulting in a degradation of the ECoG signals.

9. The system of claim 8, wherein the low-power DSP (105) has an adaptive power management unit for placing components of which the chest wall unit is comprised, including said adaptive power management unit, into a sleep mode when not in use.

10. The system of claim 8, wherein the low-power RF TRX (109) is dual mode, wherein a first mode is a high data rate transmission mode and a second mode is a low data rate transmission mode.

11. The system of claim 8, wherein the prosthetic is attached to an upper or lower extremity of the patient to enable movement of said extremity.

12. The system of claim 8, wherein the prosthetic is a robotic gait exoskeleton ("RGE') or a functional electrical stimulation ("FES") system.

13. The system of claim 10, wherein the plurality of real-time commands is wirelessly transmitted to the prosthetic via the low-power RF TRX (109) operating in the second mode.

14. The system of claim 10, wherein the data set is wirelessly transmitted to the external computer for processing via the low-power RF TRX (109) operating in the first mode, wherein the external computer processes the data set via one or more decoding models to generate the plurality of real-time commands, which are transmitted to the prosthetic for execution.

15. The system of claim 8, wherein the plurality of real-time commands generated via the low-power DSP (105) are stored by the memory module (107).

16. The system of claim 8, wherein the ULP amplifier array (106) is a 64-channel ULP amplifier array.

17. The system of claim 8, wherein a wireless charging coil (113) is operatively coupled to the battery (111) for wirelessly charging and recharging the battery (111).

\* \* \* \* \*